US00PP35571P2

(12) United States Plant Patent
Morelli

(10) Patent No.: US PP35,571 P2
(45) Date of Patent: Jan. 9, 2024

(54) ***CANNABIS* PLANT NAMED 'AC/DC X REDNECK WEDDING 13'**

(50) Latin Name: ***Cannabis* hybrid**
Varietal Denomination: AC/DC x Redneck Wedding 13

(71) Applicant: Phat Panda LLC, Spokane, WA (US)

(72) Inventor: Mojave Morelli, Colbert, WA (US)

( * ) Notice: Subject to any disclaimer, the term of this patent is extended or adjusted under 35 U.S.C. 154(b) by 0 days.

(21) Appl. No.: 18/144,106

(22) Filed: May 5, 2023

(51) Int. Cl.
*A01H 5/02* (2018.01)
*A01H 6/28* (2018.01)

(52) U.S. Cl.
USPC ..... Plt./258
CPC ..... *A01H 6/28* (2018.05)

(58) Field of Classification Search
USPC ..... Plt./258
CPC ..... A01H 5/02
See application file for complete search history.

(56) References Cited

U.S. PATENT DOCUMENTS

| | | | |
|---|---|---|---|
| 9,095,554 | B2 | 8/2015 | Lewis et al. |
| 10,499,584 | B2 | 12/2019 | Fletcher et al. |
| PP31,535 | P3 | 3/2020 | Lewis et al. |
| 10,675,264 | B2 | 6/2020 | Green et al. |
| 10,934,554 | B2 | 3/2021 | Boudko et al. |
| PP33,162 | P3 | 6/2021 | Klettke |
| PP33,332 | P3 | 8/2021 | Lewis et al. |
| 11,297,789 | B2 | 4/2022 | Kahn et al. |
| PP34,802 | P2 | 12/2022 | Schatz et al. |

*Primary Examiner* — Kent L Bell

(74) *Attorney, Agent, or Firm* — Derek Fahey, Esq.; The Plus IP Firm, PLLC

(57) ABSTRACT

The present invention provides a new and distinct *Cannabis* plant designated as 'AC/DC x Redneck Wedding 13'. The main terpenes found in 'AC/DC x Redneck Wedding 13' are myrcene, alpha-pinene, beta-pinene, and limonene. The estimated concentration of the total THC and CBD is approximately 7.10% and approximately 11.0%, respectively, at the time of assaying metabolites from flower samples of 'AC/DC x Redneck Wedding 13'. The 'AC/DC x Redneck Wedding 13' cultivar of *Cannabis* exhibits a unique combination of leaf characteristics, balanced THC and CBD levels, pleasant aroma and taste, upright monopodial growth habit, and tight, compact flowering. The upright monopodial growth habit provides several advantages for growers, including efficient use of vertical space, improved light penetration, better air circulation, and easier pruning and maintenance, which leads to higher yields.

15 Drawing Sheets

Latin name of genus and species: Latin Name of genus and species: *Cannabis* hybrid.

Variety denomination: Variety denomination: 'AC/DC x Redneck Wedding 13'.

TECHNICAL FIELD

The present disclosure relates to the field of *Cannabis* cultivar, and more specifically a new and distinct *Cannabis* cultivar designated as 'AC/DC x Redneck Wedding 13'.

BACKGROUND

*Cannabis*, a versatile and diverse genus of flowering plants, has long been cultivated and utilized for medicinal, recreational, and industrial purposes. The three primary species, *Cannabis sativa, Cannabis indica*, and *Cannabis ruderalis*, display distinct phenotypes and secondary metabolite profiles, contributing to the unique properties associated with each species. The increasing global interest in *Cannabis* has spurred the development of breeding programs to create new cultivars with specific traits to address consumer demands, adapt to various environmental conditions, and comply with regulatory requirements.

Historically, *Cannabis* has been cultivated for fiber production, medicinal applications, and as a psychoactive substance. The plant's pharmacological properties are attributed to the presence of various cannabinoids, such as tetrahydrocannabinol (THC) and cannabidiol (CBD), which have been extensively studied and documented. Recent advancements in research and the growing acceptance of *Cannabis* for medical use have led to a surge in interest in breeding *Cannabis* cultivars with specific cannabinoid profiles to target various medical conditions effectively.

Apart from cannabinoid content, *Cannabis* cultivars can exhibit a diverse range of other characteristics, including growth habit, plant size, morphology, resistance to pests and diseases, flowering time, and terpene profile. These traits are influenced by genetic factors, environmental conditions, and cultivation practices. As the *Cannabis* industry continues to expand and evolve, the need for novel cultivars with unique and desirable traits becomes increasingly important.

Modern breeding efforts have resulted in the development of hybrid *Cannabis* cultivars that combine the desirable traits of different *Cannabis* species. These hybrids often exhibit a blend of characteristics, such as the vigorous growth and high cannabinoid content of *Cannabis sativa*, coupled with the compact structure and adaptability to temperate climates of *Cannabis indica*. However, the development of new and distinct cultivars remains challenging due to the complex nature of *Cannabis* genetics and the ongoing debates surrounding its taxonomy and nomenclature.

Understanding the genetic basis of *Cannabis* traits is essential for the development of novel cultivars. Advances in genomics and molecular biology have provided breeders with tools to identify key genes and genetic markers associated with desirable traits. These tools facilitate the selection of parental plants and the evaluation of progeny, allowing for more efficient breeding processes and the development of cultivars with tailored characteristics.

SUMMARY

A new and distinct *Cannabis* cultivar being of Latin name of genus and species, *Cannabis* hybrid, and designated as 'AC/DC x Redneck Wedding 13' is disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

The present invention relates to the development of a new and distinct *Cannabis* cultivar that possesses a unique combination of traits not found in existing *Cannabis* varieties known to the Inventor. This novel cultivar aims to address the growing demand for tailored *Cannabis* cultivars with specific morphological, physiological, and chemical properties for various applications, including therapeutic, medicinal, and commercial purposes.

As used herein, the term "cultivar" is used interchangeably with "variety", "strain", and/or "clone". *Cannabis* plants produce a unique family of terpenophenolic compounds. Cannabinoids, terpenoids, and other compounds are secreted by glandular trichomes that occur most abundantly on the floral calyxes and bracts of female plants. As a drug it usually comes in the form of dried flower buds (marijuana), resin (hashish), or various extracts collectively known as hashish oil. The *Cannabis* plant has at least 545 distinct compounds that span 20 chemical classes including cannabinoids, terpenes, terpenoids, amino acids, nitrogenous compounds, simple alcohols, aldehydes, ketones, esters, lactones, acids, fatty acids, steroids, noncarmabinoid phenols, pigments, flavonoids, vitamins, proteins, enzymes, glycoproteins, and hydrocarbons. Terpenes and/or cannabinoids, in particular, have shown great potential in terms of medicinal value. Terpenes and/or cannabinoids have been shown to be largely responsible for beneficial effects of a *Cannabis* plant. In fact, each *Cannabis* plant has the varying concentrations of medically viable compounds depending on different strains (genotypes) and their resulting chemotypes. Even a small variation in terpene and/or cannabinoid concentration can cause noticeable differences in the entourage and/or synergistic effects of a *Cannabis* plant, which distinguishes one variety from another. Research shows that it relies heavily on the physiological effects produced by terpenes and/or cannabinoids.

Terpenes are a large and diverse class of organic compounds, produced by a variety of plants. They are often strong smelling and thus may have had a protective function. Terpenes are an important component, not only influencing taste and smell of each *Cannabis* strain but also influencing its effects on the mind and body of a subject such as humans and animals. Terpenes are a classification of organic molecules that are found in a wide variety of plants and animals. These molecules are known for their characteristic scents and flavors. The varying terpene concentrations found in *Cannabis* plants directly influence the resulting taste and smell, as well as the observed effects. Non-limiting examples of terpenes include Hemiterpenes, Monoterpenes, Sesquiterpenes, Diterpenes, Sesterterpenes, Triterpenes, Sesquarterpenes, Tetraterpenes, Polyterpenes, and Norisoprenoids. The main terpenes found in *Cannabis* plants include, but are not limited to, myrcene, limonene, caryophyllene, pinene, terpinene, terpinolene, camphene, terpineol, phellandrene, carene, humulene, pulegone, sabinene, geraniol, linalool, fenchol, borneol, eucalyptol, and nerolidol. Over 100 different kinds of terpenes have been identified in *Cannabis* plants although not being as well-studied as cannabinoids, they are instrumental in giving rise to the physiological and psychoactive effects in *Cannabis*.

Cannabinoids are the most studied group of the main physiologically active secondary metabolites in *Cannabis*. The classical cannabinoids are concentrated in a viscous resin produced in structures known as glandular trichomes. At least 113 different cannabinoids have been isolated from *Cannabis* plants. The main classes of cannabinoids from *Cannabis* include tetrahydrocannabinol (THC), cannabidiol (CBD), cannabigerol (CBG), and cannabinol (CBN). Cannabinoid can be at least one of a group comprising tetrahydrocannabinol (THC), cannabidiol (CBD), cannabigerol (CBG), cannabinol (CBN) cannabichromene (CBC), cannabinodiol (CBDL), cinnabicyclol (CBL), cannabivarin (CBV), tetrahydrocannabivarin (THCV), cannabidivarin (CBDV), cannabigerovarin (CBGV), cannabichromevarin (CBCV), cannabigerol monomethyl ether (CBGM), cannabielsoin (CBE), cannabicitran (CBT), cannabinol propyl variant (CBNV), cannabitriol (CBO), tetrahydrocannabinolic acid (THCA), tetrahydrocannabivarinic acid (THCVA), cannabidiolic acid (CBDA), cannabigerolic acid (CBGA) and cannabinerolic acid.

Additionally, the biologically active chemicals found in plants, phytochemicals, may affect the normal structure or function of the human body and in some cases treat disease. The mechanisms for the medicinal and psychoactive properties of a *Cannabis* plant, like any medicinal herb, produce the pharmacologic effects of its phytochemicals, and the key phytochemicals for a medical *Cannabis* plant are cannabinoids and terpenes.

Delta-9-tetrahydrocannabinol (THC) is one of the most well-known and abundant phytocannabinoids found in the *Cannabis* plant. THC is responsible for the psychoactive effects commonly associated with *Cannabis* use, and it has been the subject of extensive research in recent years due to its potential therapeutic benefits. THC affects the brain and nervous system by binding to cannabinoid receptors, which are part of the endocannabinoid system. The endocannabinoid system plays a critical role in regulating a wide range of physiological processes, including pain, appetite, mood, and immune function.

THC primarily binds to CB1 receptors, which are found throughout the brain and nervous system. These receptors are particularly abundant in areas of the brain that are involved in regulating memory, emotion, and motor coordination, such as the hippocampus, amygdala, and basal ganglia. When THC binds to CB1 receptors, it activates a cascade of cellular signaling pathways that lead to the release of neurotransmitters, including dopamine and serotonin. This can produce a range of effects, including euphoria, relaxation, altered perception, and altered motor coordination. In addition to its effects on the brain and nervous system, THC can also affect other systems in the body, including the immune system and the cardiovascular system.

As a result, THC has been shown to have potential therapeutic benefits for a wide range of conditions, including chronic pain, nausea and vomiting, muscle spasms, and seizures. In particular, THC has been found to be effective in reducing pain and spasticity in patients with multiple sclerosis and reducing nausea and vomiting in patients undergoing chemotherapy. Studies have also shown that THC may have potential uses in the treatment of psychiatric conditions such as anxiety and depression. THC has been shown to have anxiolytic properties, and it may be effective in reducing symptoms of anxiety in certain patients.

The range of percentage of THC in *Cannabis* strains can vary widely depending on several factors, including genetics, growing conditions, and harvesting techniques. THC potency is typically measured as a percentage of the total weight of the dried plant material, with higher percentages indicating more potent strains. In general, most *Cannabis* strains fall within a THC potency range of 10% to 25%. However, some strains can have THC concentrations as low as 5% or as high as 30% or more. Strains with THC concentrations above 20% are often considered to be "high-potency" strains and are typically associated with stronger psychoactive effects.

It is worth noting that the potency of a *Cannabis* strain is not the only factor that influences its effects. The composition of other cannabinoids and terpenes present in the strain can also impact its effects and therapeutic potential. For example, strains high in CBD may have less potent psychoactive effects despite having a high THC content. Furthermore, individual responses to THC can vary greatly, and factors such as dosage, method of consumption, and individual tolerance can also impact the effects of THC on the body and mind. Therefore, it is important to approach *Cannabis* use with caution and to consult with a healthcare provider before using *Cannabis* for medicinal purposes.

Cannabidiol (CBD) is one of the principal cannabinoids found in a *Cannabis* plant and is largely considered to the most medically significant. CBD occurs in many strains, at low levels, <1%. In some cases, CBD can be the dominant cannabinoid, as high as 15% by weight. CBD is nonpsychoactive, meaning that unlike THC, CBD does not cause a noticeable "high". CBD has shown potential for the treatment of a wide variety of diseases and symptoms, including cancer, nausea, chronic pain, spasms, seizures/epilepsy, anxiety, psoriasis, Crohn's disease, rheumatoid arthritis, diabetes, schizophrenia, post-traumatic stress disorder (PTSD), alcoholism, strokes, Multiple Sclerosis, and cardiovascular disease. CBD also has been reported to act as a muscle relaxant, antibiotic, anti-inflammatory, and bone stimulant, as well as to improve blood circulation, cause drowsiness, and protect the nervous system.

A new and distinct cultivar exhibiting the THC and CBD profile of the *Cannabis* cultivar designated herein as 'AC/DC x Redneck Wedding 13' has the potential to provide therapeutic benefits without the psychoactive effects commonly associated with high-THC strains. CBD has been shown to have potential therapeutic benefits for a wide range of conditions, including chronic pain, anxiety, and epilepsy. CBD is a non-psychoactive compound found in the *Cannabis* plant that can modulate the effects of THC and other cannabinoids. Studies have shown that CBD can reduce the psychoactive effects of THC and may help to counteract some of the negative side effects associated with high-THC strains, such as anxiety and paranoia. In addition to its potential therapeutic benefits, a *Cannabis* plant with a higher CBD content and lower THC content may also be more accessible to patients who are new to *Cannabis* use or who have a low tolerance for THC. These patients may be more sensitive to the psychoactive effects of THC and may benefit from a strain with a lower THC content. Overall, a *Cannabis* plant with a higher CBD content and lower THC content may provide a balance of therapeutic benefits and accessibility, allowing patients to experience the potential therapeutic benefits of *Cannabis* without the psychoactive effects commonly associated with high-THC strains.

It can provide relief for chronic pain due to muscle spasticity, convulsions and inflammation, as well as effective relief from anxiety-related disorders. It can offer relief for patients with Multiple Sclerosis (MS), Fibromyalgia and Epilepsy. CBD has also been shown to inhibit cancer cell growth when injected into breast and brain tumors in combination with THC. A *Cannabis* cultivar can be used to achieve the desire of patients to be treated with CBD without the adverse side effects (e.g., psychoactivity) of THC.

The progenies resulting from any selection stage of either the crossing, selfing or backcrossing versions of the breeding regimes of the present invention were asexually reproduced to fix and maintain the desirable THC content, CBD content, terpenes content, the aroma and flavors typical of the desired class, and the other desirable phenotypic and/or genotype characteristics. The resultant selected *Cannabis* cultivar is designated as 'AC/DC x Redneck Wedding 13' disclosed herein.

In particular, the new *Cannabis* cultivar exhibits a set of distinct characteristics that include, but are not limited to: (i) a unique growth habit and morphology, resulting in a compact, bushy structure with high adaptability to different cultivation environments; (ii) rapid vegetative growth and a short flowering period, which allows for efficient cultivation and multiple harvests per year; (iii) high resistance to common pests and diseases, reducing the need for chemical interventions and ensuring a more sustainable cultivation process; (iv) distinctive terpene profile that contributes to a pleasant aroma and flavor, enhancing the overall consumer experience; (v) balanced and high levels of cannabinoids, such as THC and CBD, providing potential therapeutic benefits and meeting the diverse needs of the *Cannabis* market; (vi) superior performance in various cultivation methods, including indoor, outdoor, and greenhouse environments, making it suitable for a wide range of growers and cultivation conditions; (vii) enhanced environmental stress tolerance, enabling the cultivar to thrive under diverse climatic conditions and improving its overall performance and yield potential; and (viii) improved trichome density and distribution, which may contribute to increased cannabinoid and terpene production, as well as enhanced visual appeal.

The inventor propagated offspring of selected *Cannabis* asexually through stem cutting and cloning, which led to the development of this exceptional new cultivar. The plant has been and continues to be asexually propagated by means of stem cutting and cloning at the creator's greenhouses, nurseries, and/or fields in Spokane Valley, Washington.

The most notable and distinctive chemical features of this new cultivar, when cultivated under standard conditions in Spokane Valley, Washington, follows. Chemical analyses of the new *Cannabis* variety and the reference variety (or the parent varieties) were conducted using widely recognized chemical separation techniques by experts in the field. Flower tissue samples from the described *Cannabis* plant were used for testing. The cannabinoid composition of this cultivar can be ascertained by measuring the concentration of at least one cannabinoid in a portion (e.g., sample) of the harvested product.

Table 1A includes detailed information of the *Cannabis* plant named 'AC/DC x Redneck Wedding 13' including the concentration ranges of terpenes and cannabinoids as tested on flowers sampled on at least four different dates. The *Cannabis* plant has been tested in a laboratory setting and/or facility to determine cannabinoids and terpenes concentrations in the *Cannabis* plant named 'AC/DC x Redneck Wedding 13' according to the procedures provided in Giese et al. (Journal of AOAC International (2015) 98(6):1503-1522).

1) The main terpenes found in 'AC/DC x Redneck Wedding 13' are myrcene, alpha-pinene, beta-pinene, and limonene. These terpenes are present in higher concentrations compared to the other terpenes found in this cultivar, contributing to its unique aroma, flavor, and potential therapeutic properties.
2) The estimated concentration of the total THC and CBD is approximately 7.10% and approximately 11.0%, respectively, at the time of assaying metabolites from flower samples of 'AC/DC x Redneck Wedding 13'.
3) The harvest interval is 54-56 days under short day conditions.

Terpene and cannabinoid profiles of 'AC/DC x Redneck Wedding 13' demonstrate that 'AC/DC x Redneck Wedding 13' has a phenotypically unique profile, particularly insofar as to the level of terpenes and cannabinoids. This data is presented in tabular form in Table 1A below. It is understood that the ranges of active cannabinoids is +/− 2.00% by weight and terpenes is +/− 0.02% by weight of the data indicated below. The Max THX is calculated using the formula: THCmax (a.k.a. Max THC)=d9−THC+(THC−A*0.877) and the Max CBD is calculated using the formula: CBDmax (a.k.a. MaxCBD)=CBD+(CBD−A*0.877).

TABLE 1A

| Ranges of Active Cannabinoids and Terpenes | | | |
|---|---|---|---|
| Ranges of Active Cannabinoids (% by weight) | | | |
| Max THC | 7.10% | Max CBD | 11.0% |
| Terpenes (% by weight) | | | |
| thujene | 0.00% | fenchone | 0.0043% |
| alpha-pinene | 0.11% | menthone | 0.0019% |
| camphene | 0.0081% | terpineol | 0.023% |
| beta-pinene | 0.075% | trans-alpha-bergamotene | 0.005% |
| myrcene | 1.2% | beta-farnesene | 0.007% |
| alpha-phellandrene | 0.00% | alpha-farnesene | 0.027% |
| carene | 0.00% | guaiol | 0.032% |
| alpha-terpinene | 0.00% | bisabolol | 0.06% |
| limonene | 0.23% | geraniol | 0.00% |
| alpha-bulnesene | 0.0079% | geranyl-acetate | 0.00% |
| alpha-bisabolene | 0.018% | methy-eugenol | 0.00% |
| beta-maaliene | 0.01% | beta-caryophyllene | 0.00% |
| selinadiene | 0.027% | alpha-humulene | 0.036% |
| alpha-maaliene | 0.027% | cis-nerolidol | 0.00% |
| eucalyptol | 0.0026% | trans-nerolidol | 0.00% |
| terpinolene | 0.0026% | caryophyllene oxide | 0.094% |

TABLE 1A-continued

| Ranges of Active Cannabinoids and Terpenes | | | |
|---|---|---|---|
| linalool | 0.038% | alpha-bisabolol | 0.00% |
| fenchol | 0.029% | nerol | 0.00% |
| | | Total Terpenes (% by weight) | 2.10% |

The *Cannabis* plant 'AC/DC x Redneck Wedding 13' has the following active cannabinoid and terpene concentrations, as shown in Table 1A. The maximum THC concentration is 7.1% by weight, while the maximum CBD concentration is 11%. Terpenes are present in varying concentrations, totaling 2.10% by weight. Some of the more abundant terpenes include myrcene at 1.2%, alpha-pinene at 0.11%, beta-pinene at 0.075%, and limonene at 0.23%. Other terpenes, such as thujene, alpha-phellandrene, carene, and alpha-terpinene, are present in trace amounts or not detected at all. The terpene profile is diverse, contributing to the unique characteristics of the 'AC/DC x Redneck Wedding 13' cultivar.

Table 1B, below, is the cannabinoid profile of the female parental plant, 'AC/DC'. This data is presented in tabular form in Table 1B below. It is understood that the ranges of active cannabinoids is +/− 2.00% by weight. The Max THX is calculated using the formula: THCmax (a.k.a. Max THC)= d9−THC+(THC−A*0.877) and the Max CBD is calculated using the formula: CBDmax (a.k.a. MaxCBD)= CBD+(CBD−A*0.877).

TABLE 1B

| Ranges of Active Cannabinoids<br>Ranges of Active Cannabinoids (% by weight) | | | |
|---|---|---|---|
| Max THC | 1.02% | Max CBD | 20.03% |

The development of this new *Cannabis* cultivar, 'AC/DC x Redneck Wedding 13', aims to contribute to the ongoing diversification of *Cannabis* genetics and provide novel solutions for the growing *Cannabis* industry. By addressing the specific needs and preferences of consumers and cultivators alike, this cultivar is poised to become a valuable addition to the existing pool of *Cannabis* varieties.

The innovative breeding techniques employed in the creation of this cultivar are based on advances in genomics and molecular biology, as well as a deep understanding of the plant's physiology and biochemistry. These techniques enable the selection of desirable traits from various *Cannabis* species and their subsequent combination into a single, unique cultivar. The result is a plant, 'AC/DC x Redneck Wedding 13', that not only meets the demands of the modern *Cannabis* industry but also paves the way for future research and development in *Cannabis* breeding.

Furthermore, this new cultivar, 'AC/DC x Redneck Wedding 13', demonstrates the potential for the development of additional *Cannabis* varieties tailored to specific applications or market niches. As research and understanding of the *Cannabis* plant continue to progress, the potential applications of targeted breeding programs are expected to expand, resulting in a diverse array of cultivars that cater to various consumer preferences and therapeutic needs.

While the female parental strain, 'AC/DC' in Table 1B has a higher maximum CBD content compared to the new *Cannabis* plant, 'AC/DC x Redneck Wedding 13', in Table 1A, 'AC/DC x Redneck Wedding 13' has a more balanced cannabinoid profile overall. This is because 'AC/DC x Redneck Wedding 13' has a maximum THC content of approximately 7.10% by weight, which is considered a moderate level of THC, while also having a maximum CBD content of approximately 11.0% by weight. This means that the ratio of THC to CBD in 'AC/DC x Redneck Wedding 13' is more balanced compared to the female parental strain, 'AC/DC', which has a much lower THC content but a much higher CBD content.

Having a balanced cannabinoid profile can be desirable for some users, particularly for medical *Cannabis* patients who may benefit from the therapeutic effects of both THC and CBD. For example, CBD has been found to have anti-inflammatory and pain-relieving properties, while THC can help with symptoms such as nausea and vomiting, as well as stimulate appetite. Furthermore, having a balanced cannabinoid profile can also reduce the risk of adverse effects such as anxiety or paranoia that can be associated with high levels of THC. Overall, the more balanced cannabinoid profile of 'AC/DC x Redneck Wedding 13' may make it a more appealing option for some users who are seeking a well-rounded *Cannabis* experience.

In conclusion, the development of this new and distinct *Cannabis* cultivar, 'AC/DC x Redneck Wedding 13', addresses the growing demand for tailored *Cannabis* cultivars with unique combinations of morphological, physiological, and chemical properties. By harnessing the power of advanced breeding techniques and a deep understanding of *Cannabis* genetics, this cultivar offers a valuable addition to the existing range of *Cannabis* varieties and opens up new possibilities for future research and development in the field of *Cannabis* breeding.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

ASEXUAL REPRODUCTION

Asexual reproduction, also known as "cloning", is a process well known to those of ordinary skill in the art of *Cannabis* production and breeding and includes, in one example embodiment, the following steps.

Asexual reproduction of a new cultivar of *Cannabis* using stem cutting and cloning techniques involves creating genetically identical clones of a parent plant. This method of propagation is highly effective and efficient, ensuring that each clone will exhibit the desirable traits of the parent plant. To successfully propagate *Cannabis* using stem cutting and cloning techniques, several factors must be taken into consideration, including temperature, soil conditions, and nutrient levels.

The first step in the process is to select a healthy and vigorous parent plant that exhibits the desired traits. The parent plant should be free of pests and diseases, and it is important to take cuttings from a plant that is in the vegetative stage of growth. The cuttings should be taken from the top of the plant or ends of the main branches, as these are the most vigorous and will produce the best clones. The ideal cutting for a clone is between five to six inches long and should leave behind at least two side branches on the main branch. The cutting should be approximately halfway in between two nodes on the main branch.

Once the cuttings have been taken, the cuttings are prepped for consistent growth. The main stem of the cutting is removed of any side nodes and the main stem is left with approximately 2-3 nodes of leaves at the end. The remaining foliage is then cut to the same length, having a spanning diameter of approximately 2 to 3 inches. Any remaining pistils, stipules, or calyx are removed from the cutting. The bottom of the stem of the cutting is further cut at an angle below the bottommost node, forming a new tip.

The cutting should then be immediately placed into water. Next, a proprietary rooting plug is formed to promote the development of new roots. Generally, a rooting plug is a small, pre-formed growing medium used in plant propagation to clone a plant. It is designed to support the cutting of a stem or leaf from a parent plant and to provide the necessary environment for the development of roots.

Rooting plugs are usually made of materials such as peat moss, rock wool, or coco coir, and are shaped into a compact plug that is typically 1-2 inches in diameter and 1-2 inches deep. They come with pre-made holes to insert the cutting, which ensures the cutting remains upright and stable in the plug. Rooting plugs provide a sterile environment for cuttings and create ideal conditions for the formation of new roots. Rooting plugs can be transplanted into a larger container or directly into the ground, depending on the plant's needs.

Once the cuttings have developed a strong root system and have started to produce new growth, they can be transplanted into larger containers with a well-balanced nutrient mix. It is important to monitor nutrient levels closely, as clones have a higher nutrient demand than mature plants. To maintain consistent growth of the cuttings so that they mature into ideal specimen for harvest, the growing conditions may be maintained, for example, using the methods and systems as described in U.S. Pat. No. 11,310,965 B1 issued Apr. 26, 2022 and U.S. Pat. No. 11,641,812 issued May 9, 2023 where are hereby incorporated by reference.

In conclusion, asexual preproduction of a new cultivar of *Cannabis* using stem cutting and cloning techniques is a highly effective method of propagation. To ensure successful propagation, it is important to select a healthy and vigorous parent plant, maintain the appropriate temperature and humidity levels during the rooting phase, and monitor nutrient levels closely throughout the growth cycle. By following these steps, growers can produce large numbers of genetically identical clones of 'AC/DC x Redneck Wedding 13' with predictable and desirable characteristics, ensuring a consistent supply of high-quality *Cannabis* plants for medicinal, therapeutic, and commercial use.

BRIEF DESCRIPTION OF THE DRAWINGS

The accompanying color photographs depict characteristics of the new 'AC/DC x Redneck Wedding 13' plants as nearly true as possible to make color representations. The overall appearance of the 'AC/DC x Redneck Wedding 13' plants in the photographs is shown in the colors that may differ slightly from the color values described in the detailed botanical description.

DETAILED BOTANICAL DESCRIPTION

Figure 1:
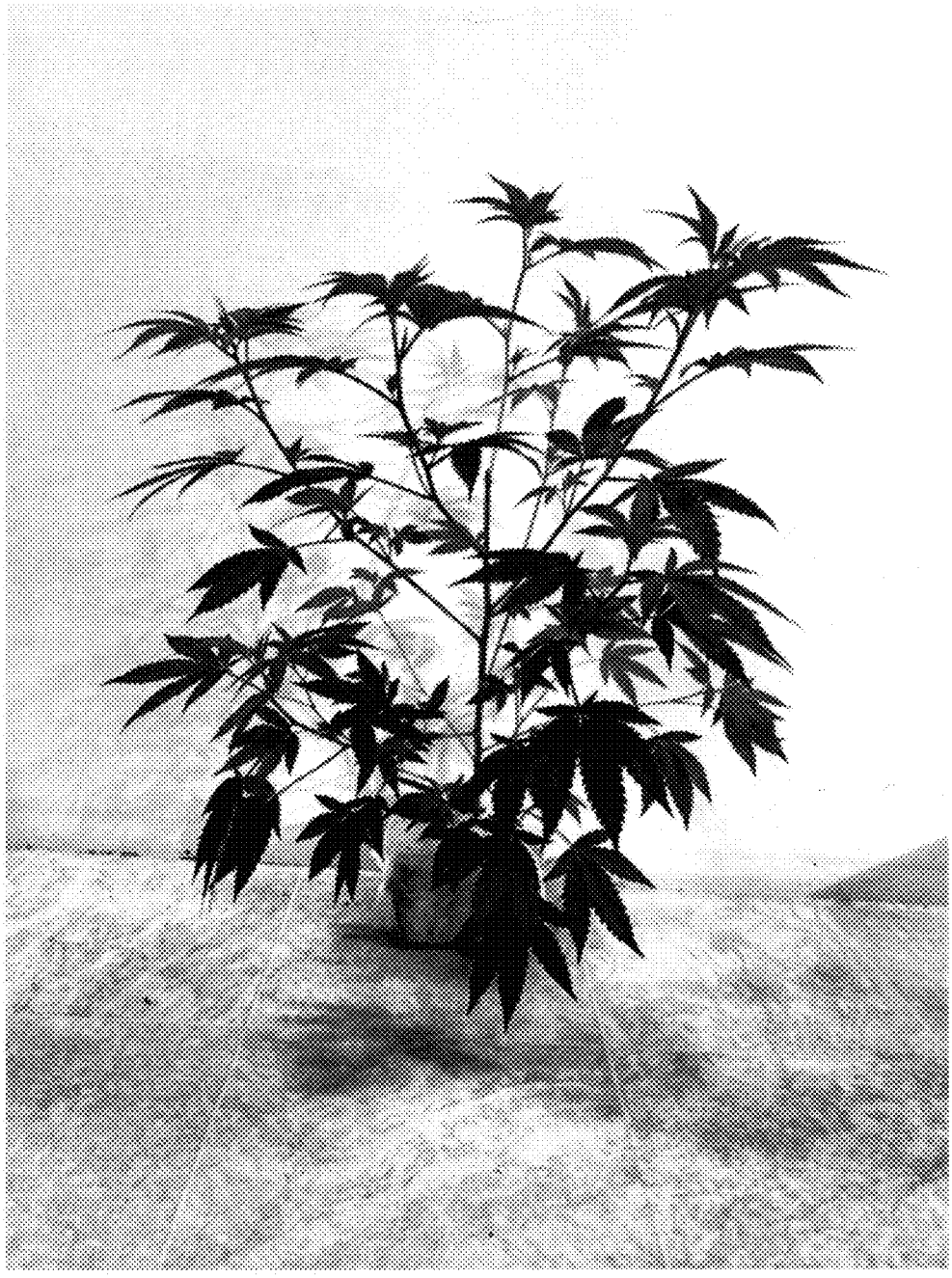
FIG. 1 is a side view of the 'AC/DC x Redneck Wedding 13' plant.
Figure 2:
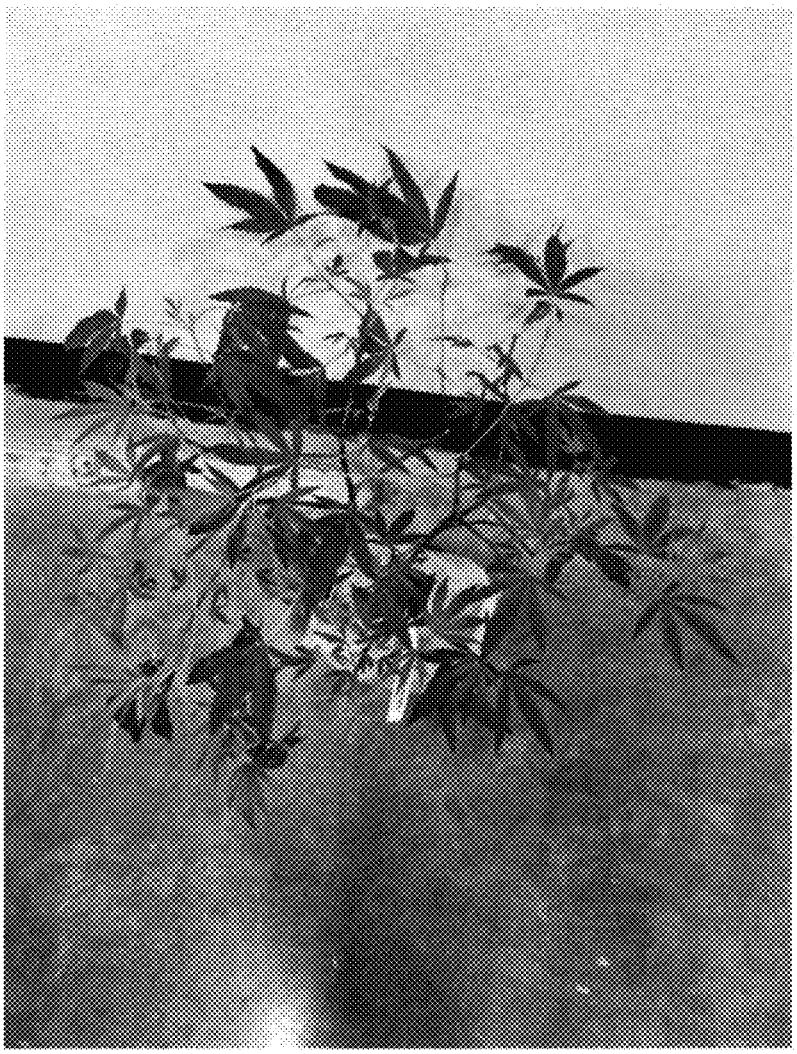
FIG. 2 is a top view of the female parental cultivar denominated as 'AC/DC' (pollen accepter; female parent).
Figure 3:
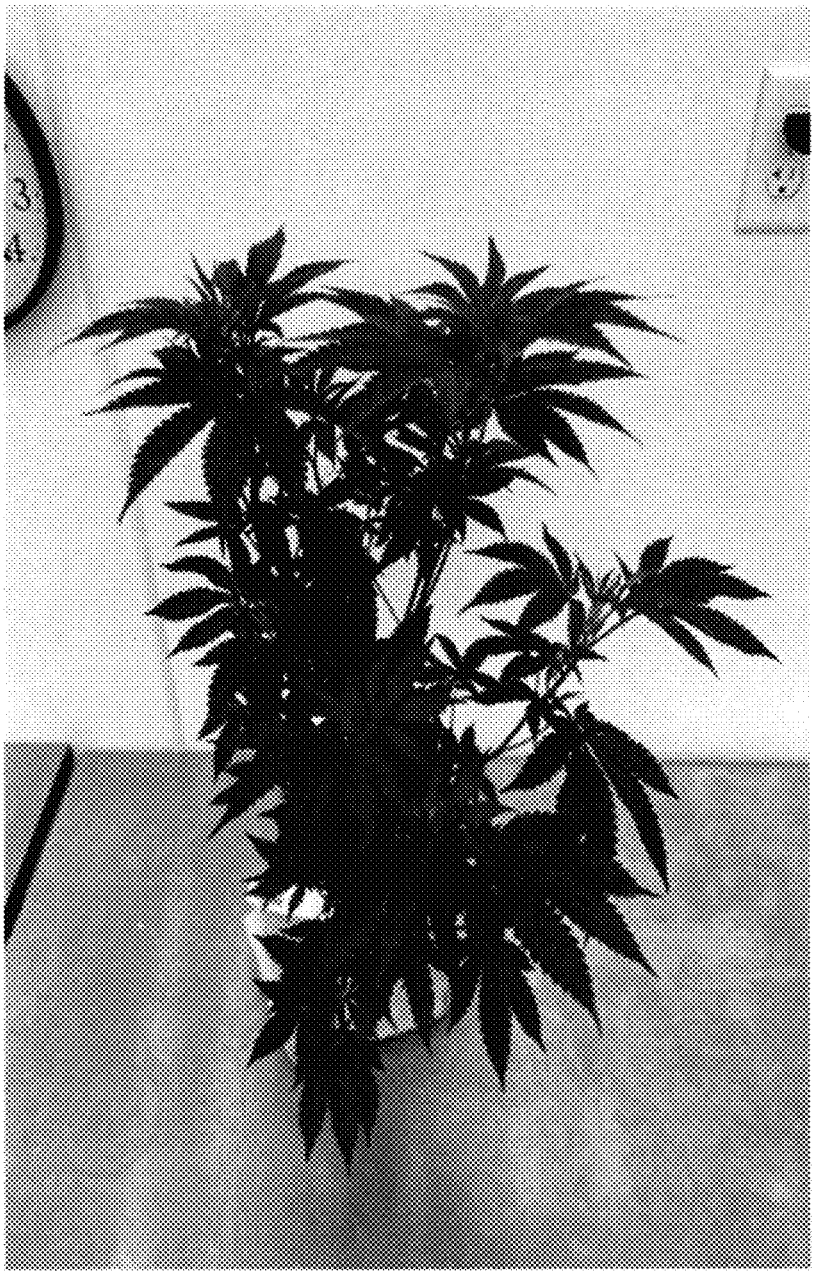
FIG. 3 is an overall view of the male parental cultivar denominated as 'Redneck Wedding' (pollen donor; male parent) from above.
Figure 4:
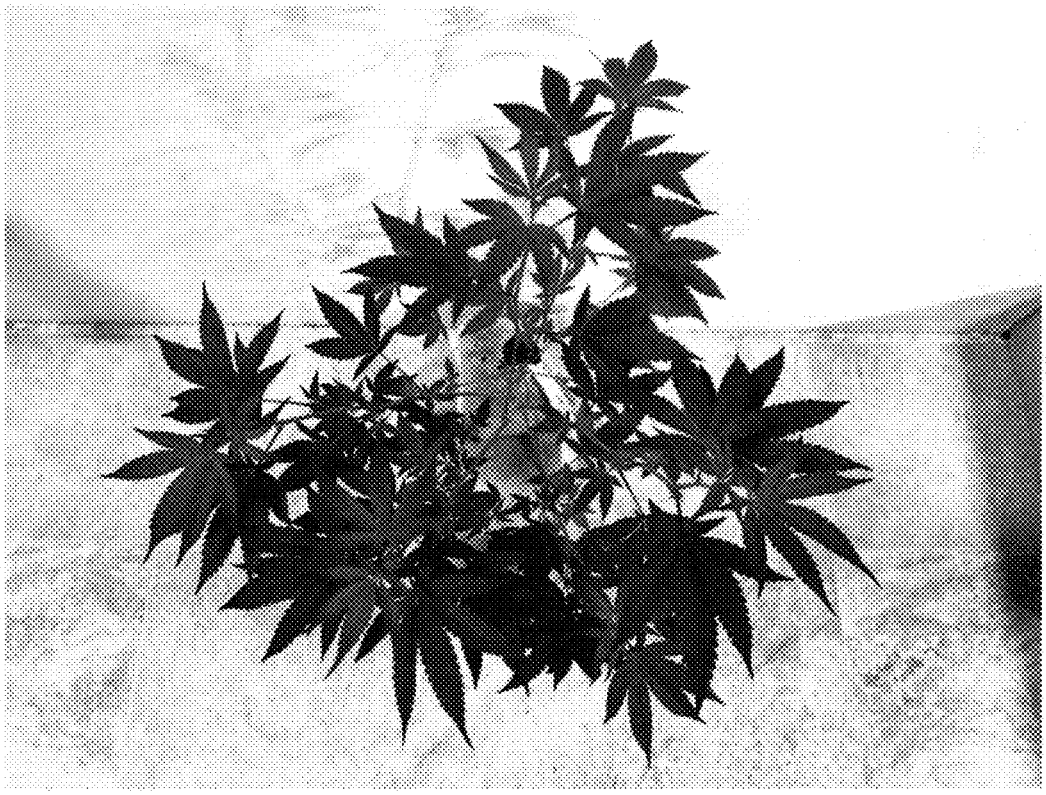
FIG. 4 is a top view of the 'AC/DC x Redneck Wedding 13' plant.
Figure 5A:
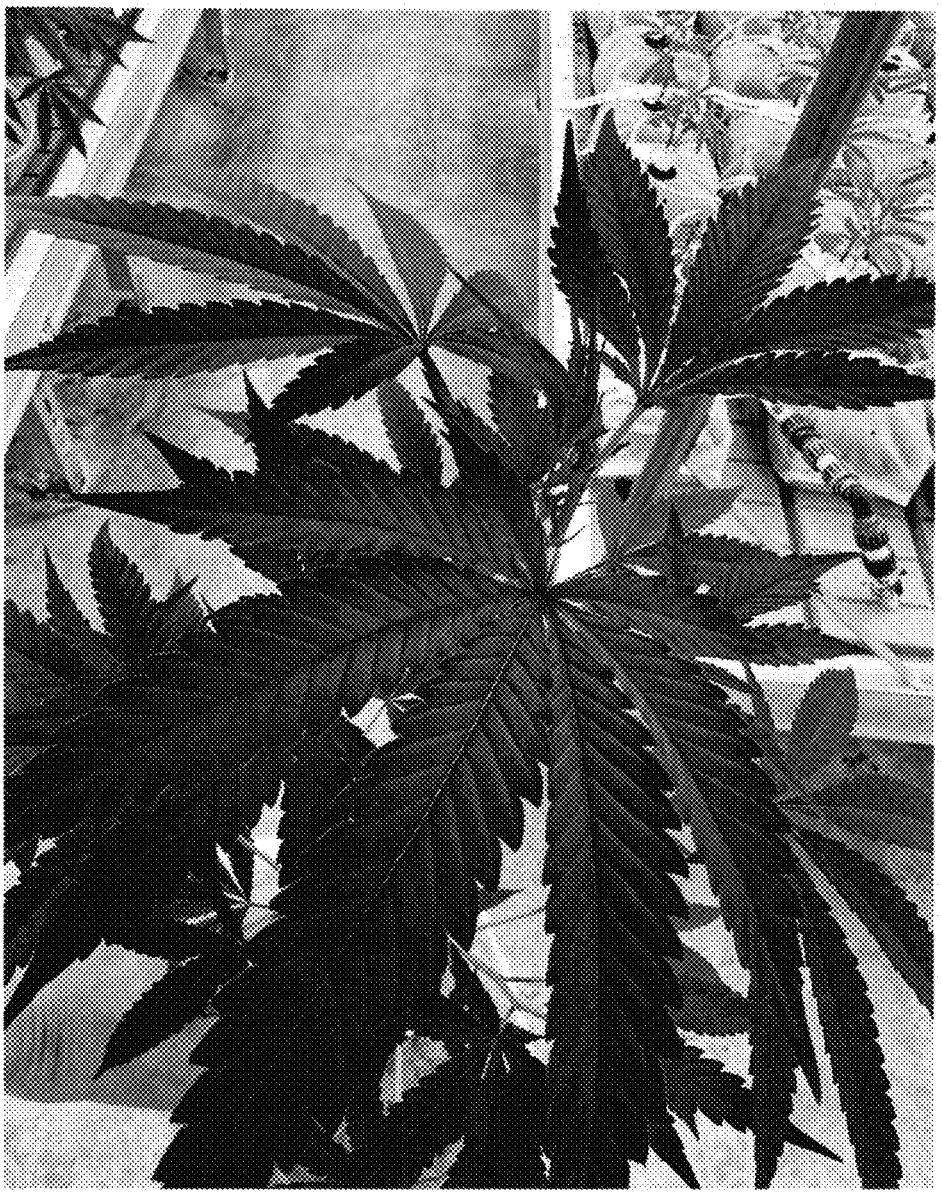
FIG. 5A is a top view of the 'AC/DC x Redneck Wedding 13' plant showing the leaf characteristics.
Figure 5B:
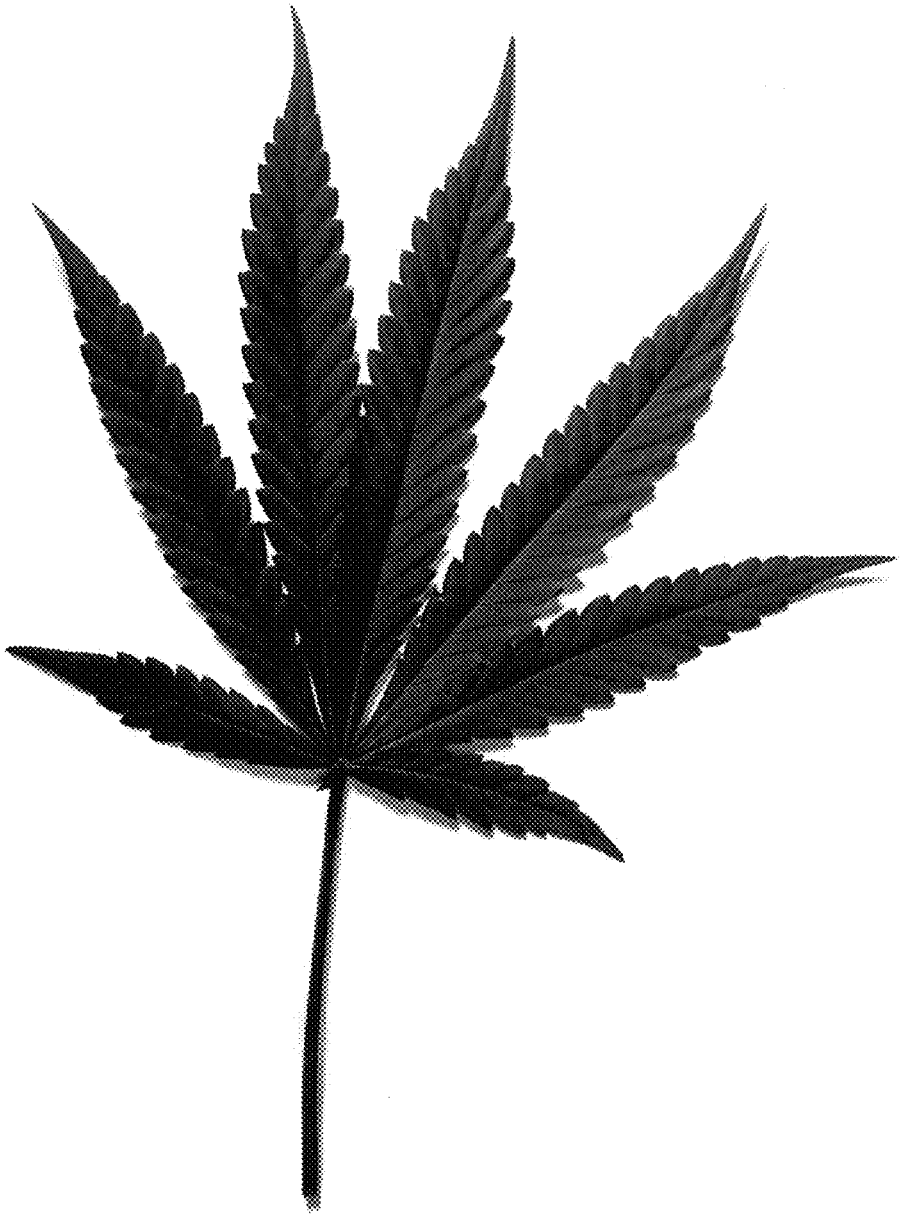
FIG. 5B is a second top view an isolated leaf of the 'AC/DC x Redneck Wedding 13' plant.
Figure 6A:
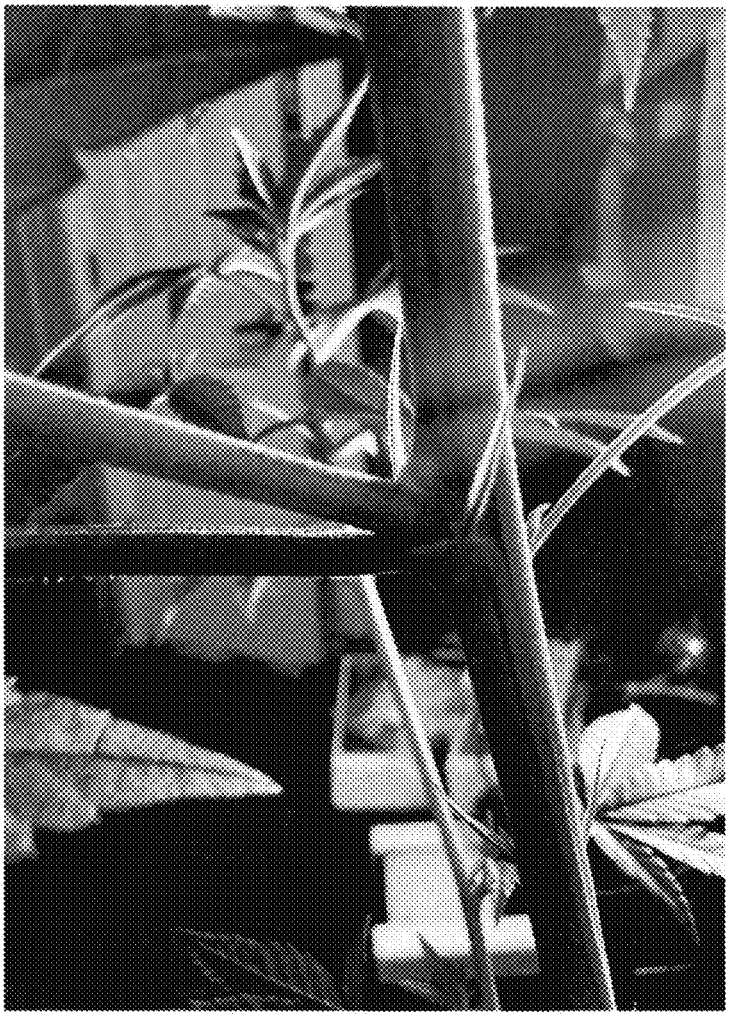
FIG. 6A is a detailed side view a node of the stem of the 'AC/DC x Redneck Wedding 13' plant showing the stem characteristics.
Figure 6B:
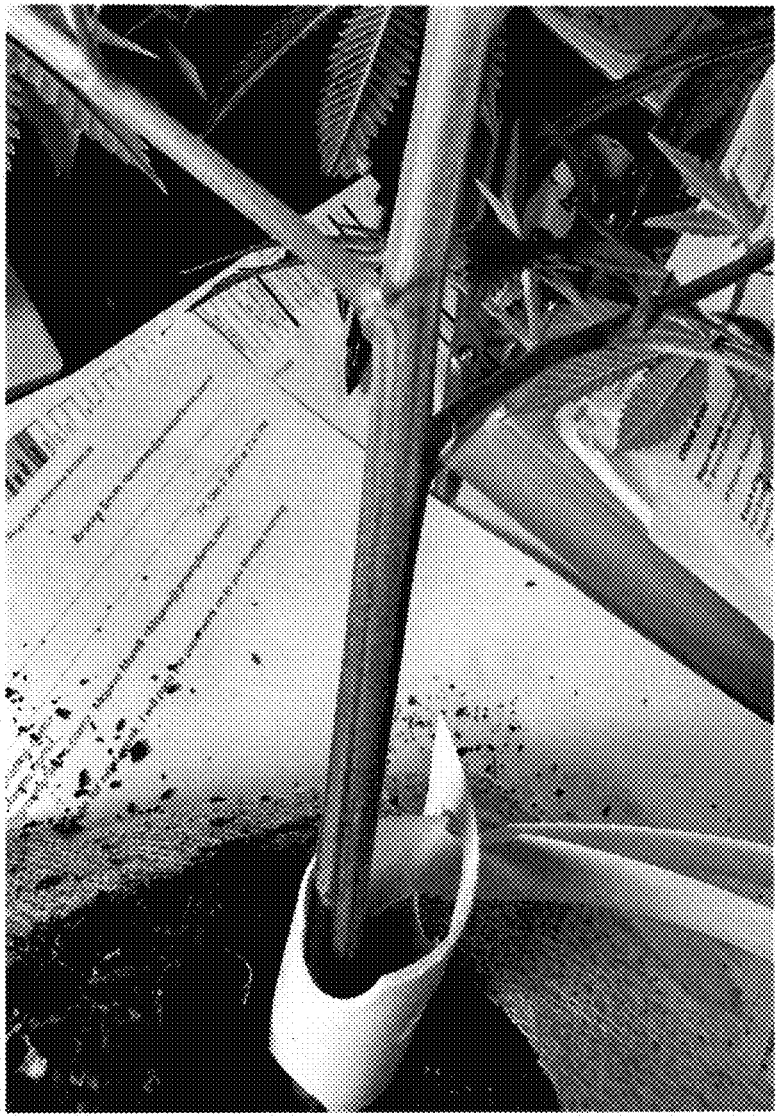
FIG. 6B is a detailed side view of the base of the 'AC/DC x Redneck Wedding 13' plant stem showing the stem characteristics.
Figure 7:
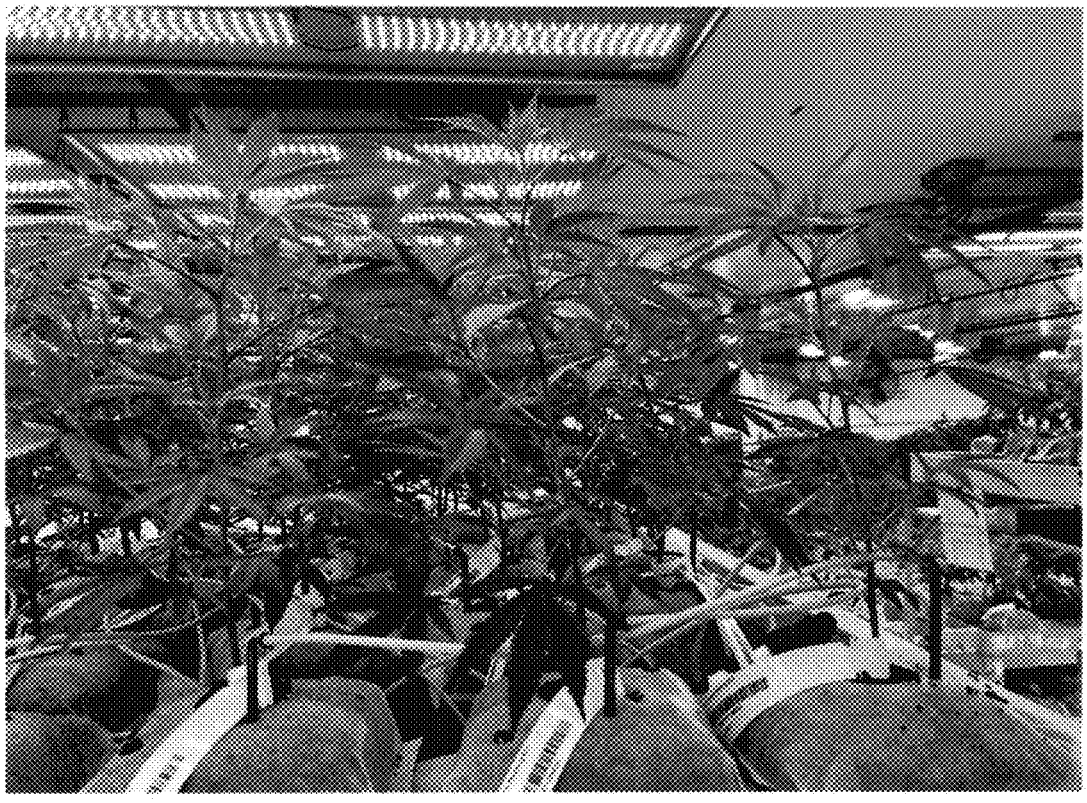
FIG. 7 is a side view of a plurality of the 'AC/DC x Redneck Wedding 13' plants at day 17 during its vegetative stage.
Figure 8A:
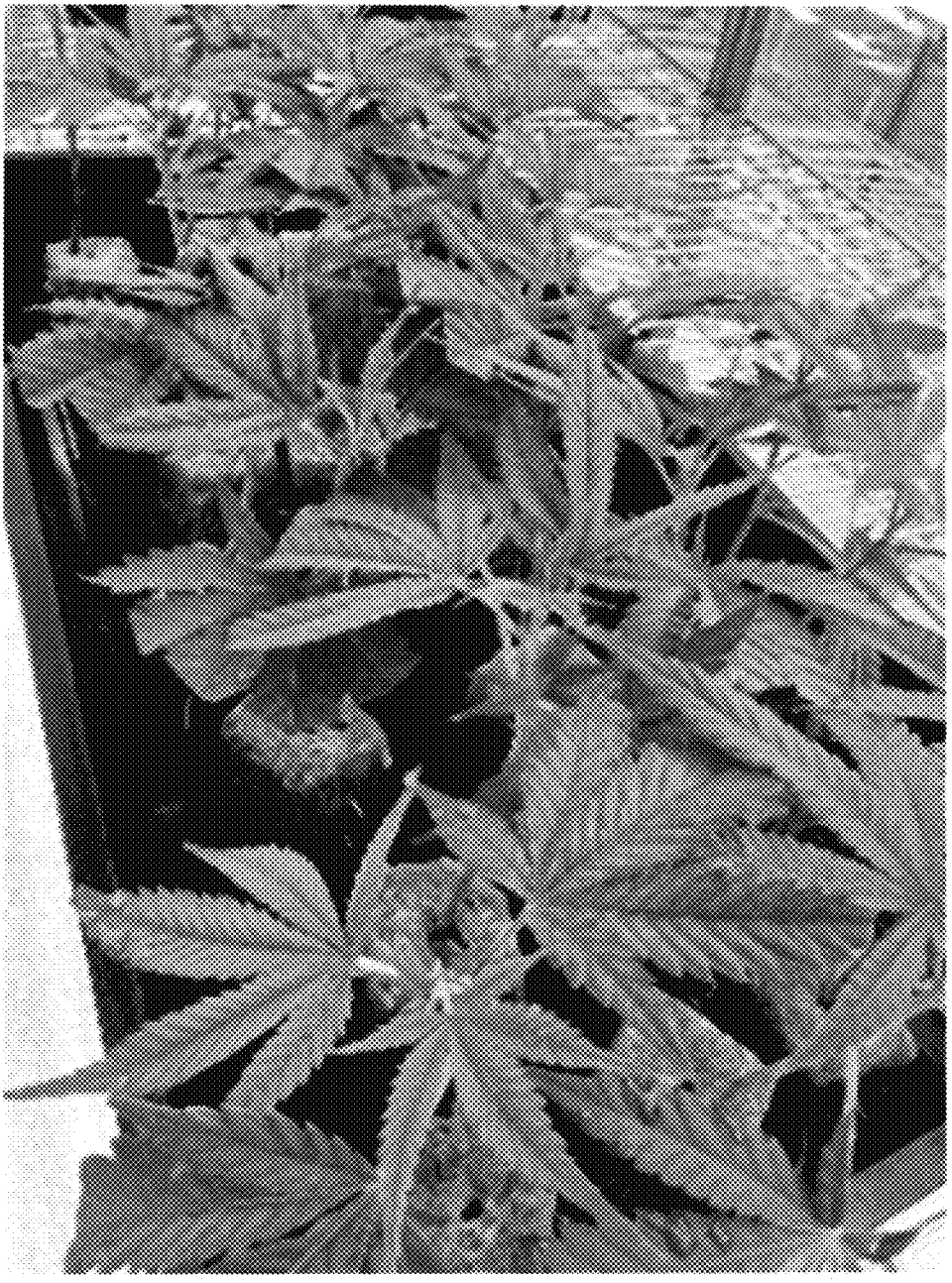
FIG. 8A is a top view a plurality of the stem cuttings of the 'AC/DC x Redneck Wedding 13' plants in the rooting plugs.
Figure 8B:
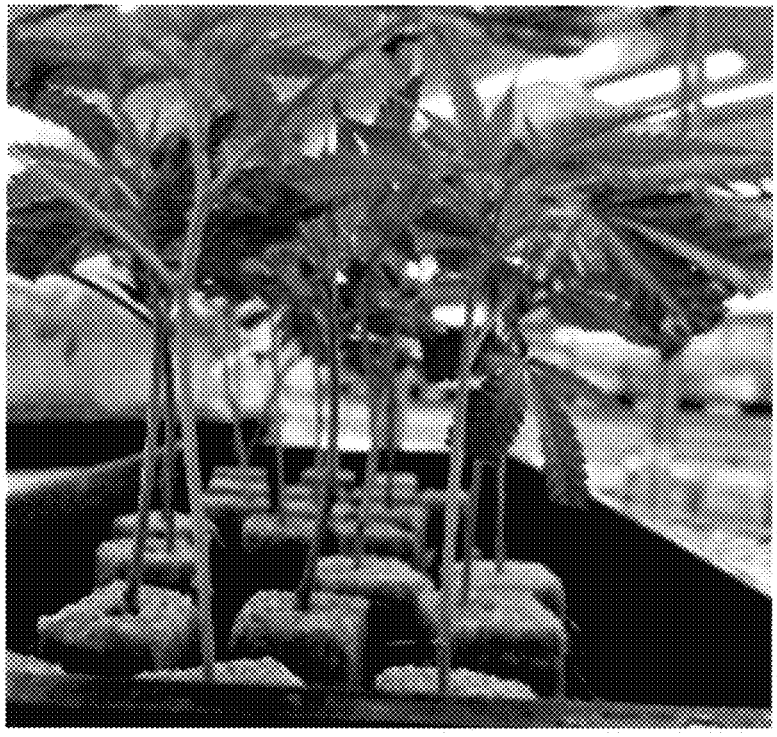
FIG. 8B is a side view of the 'AC/DC x Redneck Wedding 13' stem cuttings in the rooting plugs.
Figure 8C:
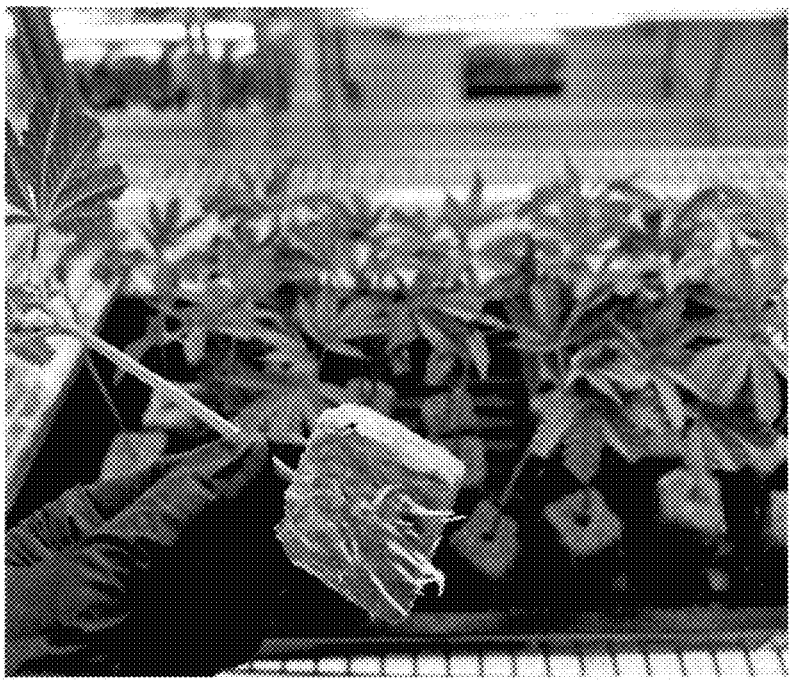
FIG. 8C is a side view of the root plug of the 'AC/DC x Redneck Wedding 13' plant exhibiting root growth.
Figure 9A:
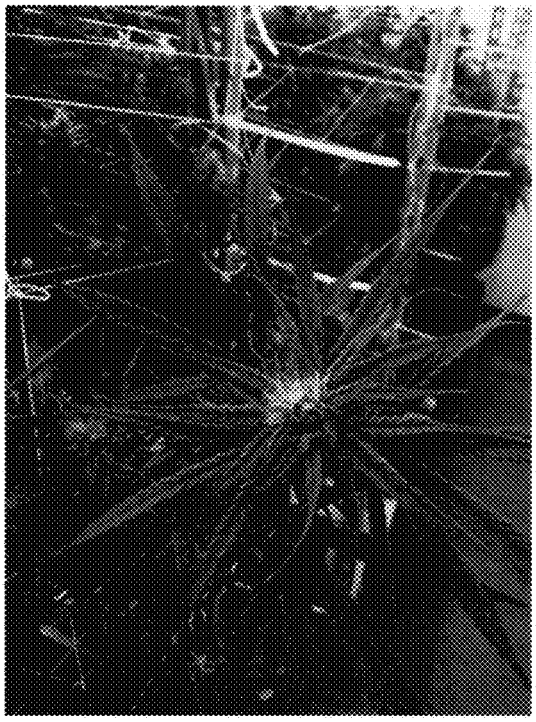
FIG. 9A is a first detailed view of the top parts (including inflorescence) of the female parental cultivar denominated as 'AC/DC' (pollen accepter; female parent) during early flowering stage from above.
Figure 9B:
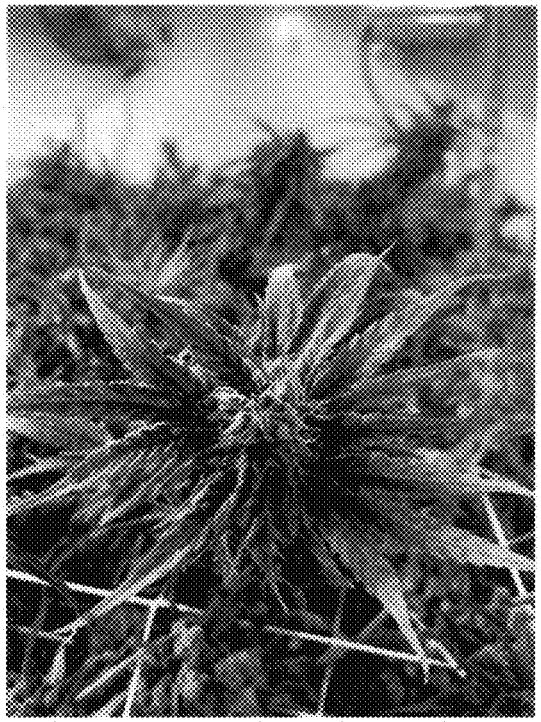
FIG. 9B is a second detailed view of the top parts (including inflorescence) of the female parental cultivar denominated as 'AC/DC' (pollen accepter; female parent) during late flowering stage from above.
Figure 9C:
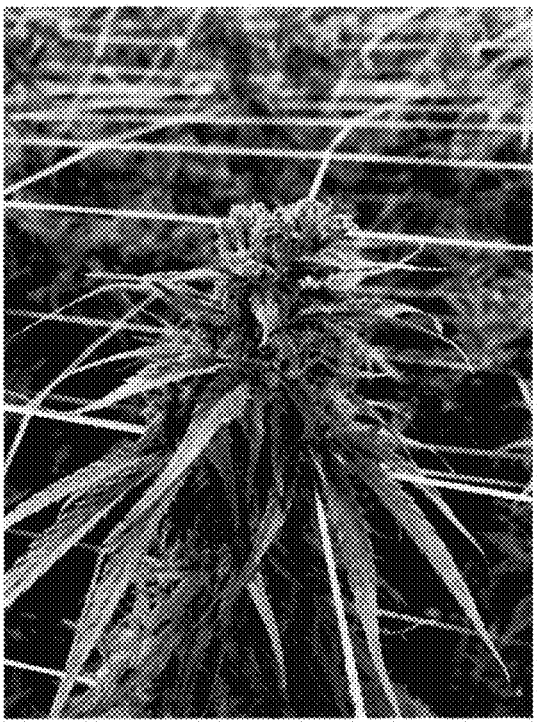
FIG. 9C is a third detailed view of the top parts (including inflorescence) of the female parental cultivar denominated as 'AC/DC' (pollen accepter; female parent) from the side.
Figure 9D:
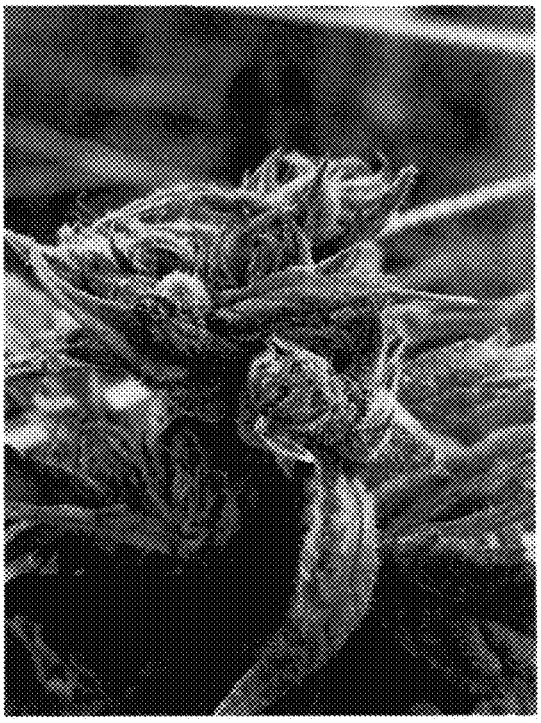
FIG. 9D is a fourth detailed view of the top parts (including inflorescence) of the female parental cultivar denominated as 'AC/DC' (pollen accepter; female parent) from the side
Figure 10:
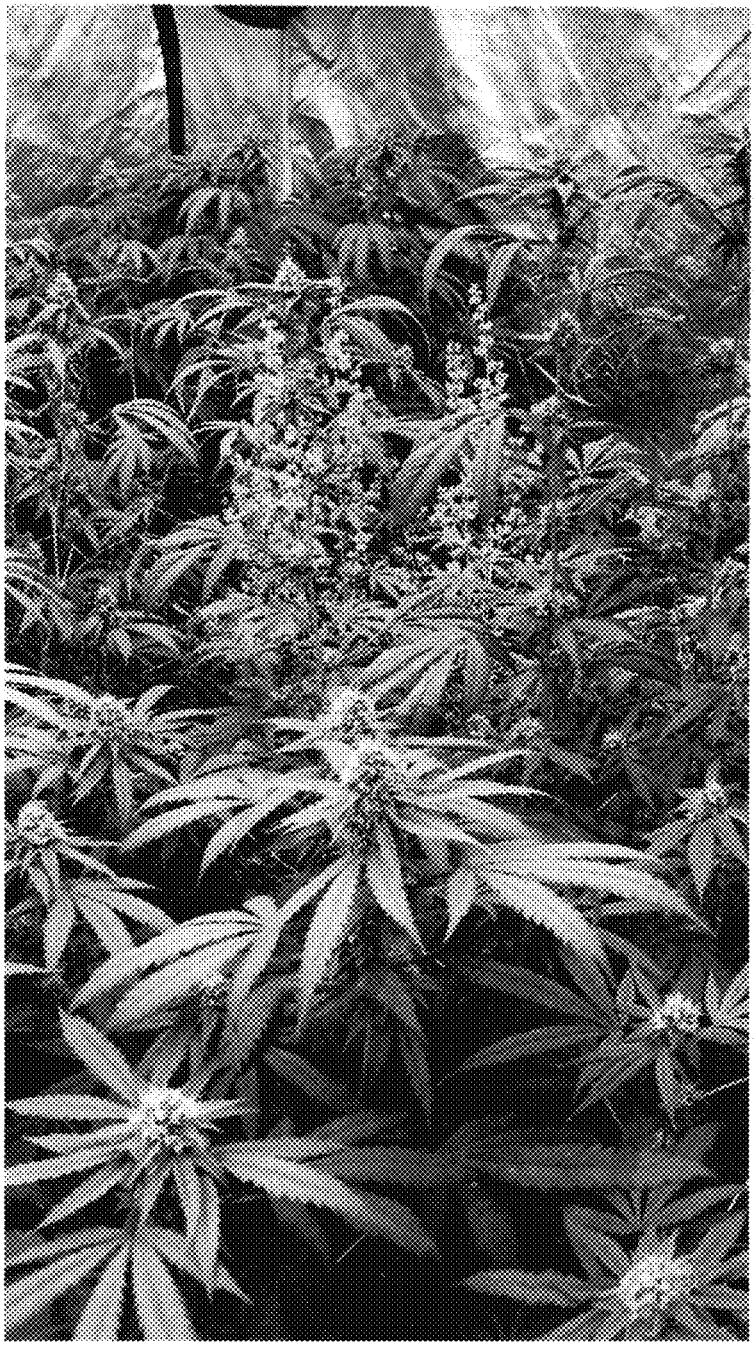
FIG. 10 shows top parts (including inflorescence) of the male parental cultivar denominated as 'Redneck Wedding' (pollen donor; male parent) from the side, the male parental cultivar being surrounded by a plurality of the female parental cultivars.
Figure 11A:
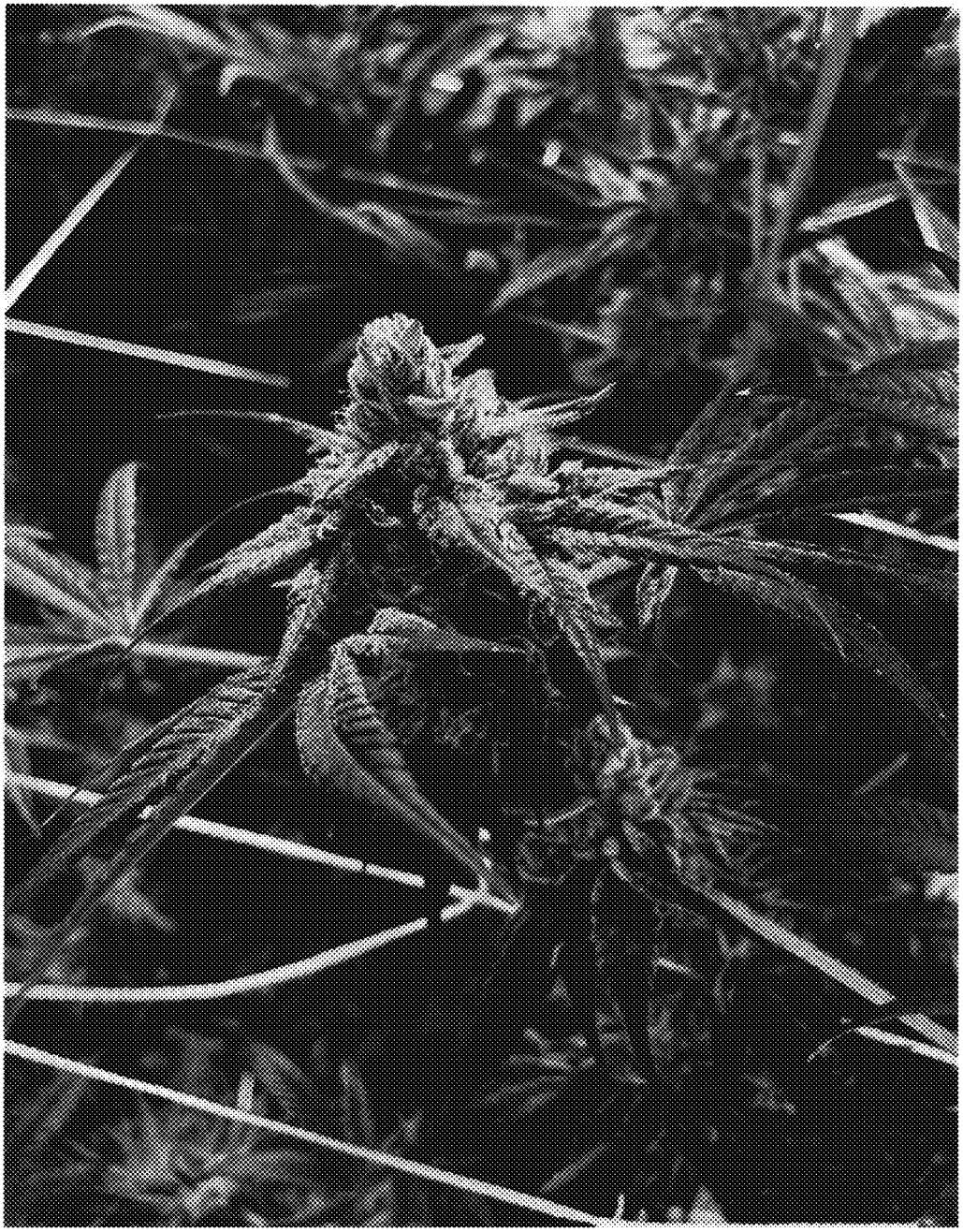
FIG. 11A is a first detailed view of top parts (including inflorescence) of the 'AC/DC x Redneck Wedding 13' plant from the side.
Figure 11B:
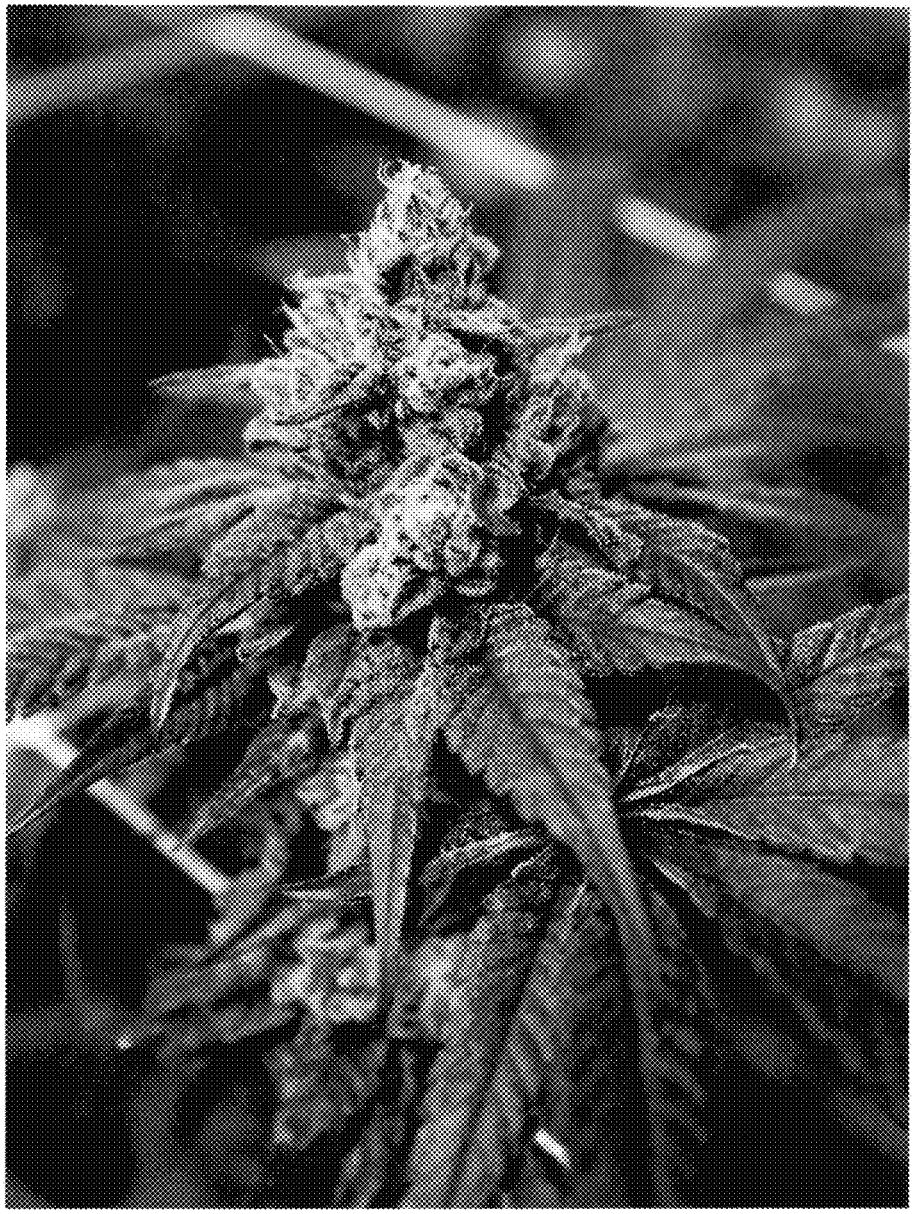
FIG. 11B is a second detailed view of top parts (including inflorescence) of the 'AC/DC x Redneck Wedding 13' plant from the side.

'AC/DC x Redneck Wedding 13' has not been observed under all possible environmental conditions, and the phenotype may vary significantly with variations in environment. The following observations, measurements, and comparisons describe this plant as grown at Salinas, Calif., when grown in the greenhouse, nursery or field, unless otherwise noted. Plants for the botanical measurements in the present application are annual plants. In the following description, the color determination is in accordance with The Royal Horticultural Society (RHS) Colour Chart, 2007 Edition, except where general color terms of ordinary dictionary significance are used. Color designations according to the RHS shall be indicated as "RHS No." for the respective color designations described herein. The *Cannabis* plant disclosed herein was derived from female and male parents that are said to have been internally designated as below. 'AC/DC x Redneck Wedding 13' is a fertile hybrid derived from a controlled cross between two proprietary cultivars denominated as 'AC/DC' (Not Patented) (pollen accepter; female parent) and 'Redneck Wedding' (Not Patented) (pollen donor; male parent). The initial cross between two parental cultivars was made in February 2022. Of the filial generation, approximately 29 seeds were germinated. The phenotypic criteria to select a new and distinct *Cannabis* cultivar disclosed herein is as follows: leaf structure having larger leaves with deep serrations, tighter flower structure, balanced THCA and CBD levels, pleasant aroma and taste. Also, the first asexual propagation by stem cuttings of 'AC/DC x Redneck Wedding 13' occurred on Jun. 5, 2022 in Spokane Valley, Washington.

The following traits in combination further distinguish the *Cannabis* cultivar 'AC/DC x Redneck Wedding 13' from check varieties, which are the female and male parents of the *Cannabis* cultivar disclosed and claimed herein. Tables 2 to 6 present phenotypic traits and/or characteristics of 'AC/DC x Redneck Wedding 13' compared to those of the parental check varieties, 'AC/DC' and 'Redneck Wedding', as follows. All plants were raised together and evaluated between 17 to 56 days old (i.e., the day range for propagation, vegetative, and flowering times). 17 days of life is the approximate end of the vegetative stage as flowering sites begin to form between days 18-21. It is further understood that the measurements in tables 2 through 6 are provided as an average measurement unless given in the form of a range or as otherwise indicated.

TABLE 2

General Characteristics

| Characteristics | New Variety | Parental Variety ('AC/DC') (Female Plant) | Parental Variety ('Redneck Wedding') (Male Plant) |
|---|---|---|---|
| Plant life forms | An herbaceous plant (herb) | An herbaceous plant (herb) | An herbaceous plant (herb) |
| Plant growth habit | An upright, tap-rooted annual plant; columnar | An upright, bushy, tap-rooted annual plant | A tall, upright, tap-rooted annual plant |
| Plant origin | 'AC/DC' × 'Redneck Wedding'; Seed | 'AC/DC' | 'Redneck Wedding' |
| Plant propagation | Asexual propagated by cloning | Asexual propagated by cloning | Asexual propagated by cloning |
| Propagation ease | Easy | Moderate | Easy |
| Average Height | 16 in at 17 days (vegetative stage); 55 in (flowering) | 23 in (vegetative stage) | 18 in (vegetative stage) |

TABLE 2-continued

| General Characteristics | | | |
|---|---|---|---|
| Characteristics | New Variety | Parental Variety ('AC/DC') (Female Plant) | Parental Variety ('Redneck Wedding') (Male Plant) |
| Average Width | 14 in at 17 days (vegetative stage); 26 in. (flowering) | 19 in (vegetative stage) | 23 in (vegetative stage) |
| Plant vigor | Moderate | Moderate | Easy |
| Time to harvest | 55 days | 56 days | N/A |
| Time to root | 9 days | N/A | N/A |
| Resistance to pest or disease | Good | Poor | Moderate |
| Disease susceptibility | Below Average; Resistant | Average to High; Susceptible to powdery mildew in the order Eyrsiphales, namely, *Erysiphe necator*, *Golovinomyces cichoracearum*, and *Oidium cannabis* | Average |
| Genetically modified organism (GMO) | No | No | No |

The new variety of *Cannabis* plant has several differences compared to its parental varieties ('AC/DC' and 'Redneck Wedding') in terms of growth, development, and resistance characteristics. While all three plants are herbaceous and propagated asexually by cloning, the new variety exhibits an upright, tap-rooted, and columnar growth habit, as opposed to the upright, bushy, tap-rooted growth habit of the female parental variety, and the tall, upright, tap-rooted growth of the male parental variety.

In terms of plant dimensions, the new variety is shorter and narrower than the parental varieties during the vegetative stage, with a height of 16 inches and a width of 14 inches at 17 days old. In comparison, the female parental variety reaches 23 inches in height and 19 inches in width, and the male parental variety reaches 18 inches in height and 23 inches in width during the vegetative stage.

A significant difference between the new variety and the parental varieties is their resistance to pests and diseases. The new variety has good pest resistance and below-average disease susceptibility, making it more resistant than the parental varieties. The female parental variety has poor pest resistance and is susceptible to powdery mildew caused by *Erysiphe necator, Golovinomyces cichoracearum*, and *Oidium cannabis*. The male parental variety has moderate pest resistance and average disease susceptibility.

The leaf morphology is of particular importance in the *Cannabis* plant, as it can provide important information about the plant's growth habits, potential yield, and other traits. In the below Table 3, a comprehensive breakdown of the leaf characteristics of the new cultivar, as well as its parent plants, is shown.

TABLE 3

| Leaf Characteristics | | | |
|---|---|---|---|
| Characteristics | New Variety | Parental Variety ('AC/DC') (Female Plant) | Parental Variety ('Redneck Wedding') (Male Plant) |
| Leaf arrangement | Normal spiraling; Alternate with average node spacing of 1.5 in at 17 days old | Normal spiraling; Alternate | Normal spiraling; Alternate |
| Leaf shape | Palmately compound with five main leaflets and two rear leaflets. | Alternate; Palmately compound with five to nine leaflets. | Alternate; Palmately compound with five to nine leaflets. |
| Leaf structure | Linear lanceolate leaflets; thin leaflets with minimal curl and minimal concavity | Linear lanceolate leaflets; thin leaflets with minimal curl and minimal concavity | Linear lanceolate leaflets; thin leaflets with minimal curl and minimal concavity |
| Leaf margins | Spread of 1.5 in to 2 in between apex of leaflets | N/A | N/A |
| Serration | Deep serration; spread of approximately 5 mm | Deep serration | Regular serration |
| Leaf hairs | Not visually present; Extremely fine | Not visually present; Extremely fine | Not visually present; Extremely fine |
| Leaf length with petiole | 8-10 in | 4 in to 5 in | 4 in to 5 in |
| Leaf width | 5 in at 17 days old | 4 in to 5 in | 4 in to 5 in |
| Petiole length | 3-5 in | N/A | N/A |
| Petiole color (PHS No.) | 59C | 59C | 59C |
| Intensity of petiole anthocyanin | Average (vegetative stage); Intense (late flowering stage) | Average (vegetative stage) | Average (vegetative stage) |
| Stipule length | 0.5 in at 17 days old | 0.5 in | 0.5 in |
| Stipule shape | Linear-lanceolate, with a narrowing tip and slight curvature | Linear-lanceolate | Linear-lanceolate |
| Stipule color (RHS No.) | 134D | 134D | 134D |
| Average No. of leaflets | 7 | 5 | 7 |
| Middle largest (longest) leaflet length | 5 in | 4 in | 4 in |
| Middle largest (longest) leaflet width | 1.5 in | 1 in | 1 in |
| Middle largest (longest) leaflet length/width ratio | 10:3 | 4:1 | 4:1 |

TABLE 3-continued

| Leaf Characteristics | | | |
|---|---|---|---|
| Characteristics | New Variety | Parental Variety ('AC/DC') (Female Plant) | Parental Variety ('Redneck Wedding') (Male Plant) |
| No. teeth of middle leaflet (average) | 45 | 40 | 40 |
| Leaf (upper side) color (RHS No.) | 135C | 135C | 135C |
| Leaf (lower side) color (RHS No.) | 135D | 135D | 135D |
| Leaf glossiness | Matte | Matte | Matte |
| Vein/midrib shape | Centrally located; Narrow-shallow on top; thick and round on underside with a depth of medium to deep | Centrally located; Narrow-shallow on top; thick and round on underside with a medium depth | Centrally located; Narrow-shallow on top; thick and round on underside with a medium depth |
| Vein/midrib color (RHS No.) | 137D | 137D | 137D |
| Aroma | Mild, slightly vinegar in leaf but strong and sweet in stem | Strong and pungent aroma that is reminiscent of a 'gassy' aroma | Bright, citrusy smell that is reminiscent of oranges, lemons, or other tart fruits and a 'tangy' aroma |

The new variety of *Cannabis*, 'AC/DC x Redneck Wedding 13' has some differences in leaf characteristics when compared to its parental varieties, 'AC/DC' female plant and 'Redneck Wedding' male plant. The new variety has a palmately compound leaf with five main leaflets and two rear leaflets, while the parental varieties have five to nine leaflets. The new variety has a larger leaf size, with a leaf length of 7 inches and a width of 5 inches at 17 days old, compared to the parental varieties with a leaf length of 4-5 inches and a width of 4-5 inches. The new variety has a slightly different aroma, being mild and slightly vinegar in the leaf but strong and sweet in the stem, while the parental varieties have a strong and pungent aroma that is reminiscent of a 'gassy' aroma and a bright, citrusy smell that is reminiscent of oranges, lemons, or other tart fruits, respectively. Overall, the new variety exhibits some distinct differences in leaf characteristics compared to its parental varieties.

Stem morphology is an important aspect of *Cannabis* plants, as it can provide valuable information about the plant's growth habits, strength, and overall health. In the below Table 4, a detailed breakdown of the stem characteristics of the new cultivar, as well as its parent plants, is shown.

TABLE 4

| Stem Characteristics | | | |
|---|---|---|---|
| Characteristics | New Variety | Parental Variety ('AC/DC') (Female Plant) | Parental Variety ('Redneck Wedding') (Male Plant) |
| Stem Shape | Rounded; ribbed | Rounded; ribbed | Rounded; ribbed |
| Stem diameter at base | 0.25 in at 17 days old (vegetative stage); 1.5 in-2 in (flowering) | 1.5 in | 1.5 in |
| Stem color (RHS No.) | 137C | 137C | 137C |
| Depth of main stem ribs/grooves | Medium to Deep | Medium | Medium |
| Strength | High | Moderate | Moderate |
| Texture | Smooth, slight elevations and raised nodules, fine hairs | N/A | N/A |
| Internode length (average) | 2 in | 1 in | 1 in |
| Node Spacing | 1.5 in to 2 in | 1 in | 1 in |
| Stem branching | Monopodial | Polychotomous | Sympodial |

The new variety of *Cannabis* plant has several differences compared to its parental varieties in terms of stem characteristics. Although all three varieties have a rounded and ribbed stem shape and share the same stem color (RHS No. 137C), there are some distinctions in their other features. First, the depth of the main stem ribs/grooves in the new variety is medium to deep, compared to the medium depth in both parental varieties. Additionally, the new variety exhibits higher stem strength compared to the moderate strength of the parental varieties. The internode length in the new variety is longer, averaging 2 inches, as opposed to the 1-inch internode length found in both parental varieties. Similarly, the node spacing in the new variety is wider, ranging from 1.5 to 2 inches, while the parental varieties have a consistent 1-inch node spacing.

Lastly, the new variety has a monopodial stem branching pattern, contrasting with the polychotomous branching of the female parental variety, 'AC/DC', and the sympodial branching of the male parental variety 'Redneck Wedding'. Monopodial stem branching can be a more desirable growth pattern in certain situations due to its various advantages for plant cultivation. Characterized by a central, dominant stem growing vertically with lateral branches emerging from the main stem, monopodial branching allows for efficient use of vertical space. This can be particularly beneficial in limited space environments, such as indoor or greenhouse cultivation. The vertical growth pattern also enables better light penetration throughout the plant, as the lateral branches tend to spread out along the main stem. Improved light distribution can lead to increased photosynthesis, overall vigor, and higher yields. Moreover, monopodial branching can provide better air circulation around the plant due to its open structure, which helps reduce the risk of fungal infections and other diseases that thrive in humid, stagnant environments. Monopodial plants are often easier to prune and maintain due to their straightforward growth pattern, and pruning can be critical for optimizing plant growth, yield, and overall health. The vertical growth and better light penetration in monopodial plants can potentially lead to higher yields, as more energy can be directed to flower and fruit production. However, the desirability of monopodial stem branching depends on the specific plant species, cultivation goals, and environmental conditions, making it essential to consider these factors when choosing between plants with different branching patterns.

Inflorescence morphology is a critical feature of *Cannabis* plants, as it can provide valuable information about the plant's potential yield, cannabinoid profile, and other important traits. In the below Table 5, a comprehensive breakdown of the inflorescence characteristics of the new cultivar, as well as its parent plants, is shown.

TABLE 5

Inflorescence (Female/Pistillate Flowers) Characteristics

| Characteristics | New Variety | Parental Variety ('AC/DC') (Female Plant) | Parental Variety ('Redneck Wedding') (Male Plant) |
|---|---|---|---|
| Flowering (blooming) habit | Indoors, blooming stage, the female cannabis plant undergoes a critical transition from vegetative growth to reproductive development, triggered by photoperiodic cues, 12 hours daylight/12 hours darkness. The plant begins to produce small, white pistils at the nodes where the leaves meet the stem, which develop into mature flowers | Indoors, blooming stage, the female cannabis plant undergoes a critical transition from vegetative growth to reproductive development, triggered by photoperiodic cues, 12 hours daylight/12 hours darkness. The plant begins to produce small, white pistils at the nodes where the leaves meet the stem, which develop into mature flowers | Indoors, blooming stage, the female cannabis plant undergoes a critical transition from vegetative growth to reproductive development, triggered by photoperiodic cues, 12 hours daylight/12 hours darkness. The plant begins to produce small, white pistils at the nodes where the leaves meet the stem, which develop into mature flowers |
| Proportion of female plants | 100% | 100% | 0% |
| Inflorescence position | Apical meristem | Apical meristem | Apical meristem |
| Flower arrangement | Raceme | Raceme | N/A |
| No. of flowers per plant | 40-50 | 50-60 | 1000+ |
| Flower shape | Compact; dense; Strobilus | Open; Spread out; Strobilus | Actinomorphic |
| Flower (individual pistillate) length | 3 in to 4 in | N/A | N/A |
| Flower diameter | 2 in to 3 in | N/A | N/A |
| Bract shape | Obovate | Obovate | Obovate |
| Bract size | ¼ in at day 17 | ¼ in (vegetative state) | ¼ in (vegetative state) |
| Bract color (RHS No.) | 140A | 140A | 140A |

TABLE 5-continued

Inflorescence (Female/Pistillate Flowers) Characteristics

| Characteristics | New Variety | Parental Variety ('AC/DC') (Female Plant) | Parental Variety ('Redneck Wedding') (Male Plant) |
|---|---|---|---|
| Calyx shape | Undulate | N/A | N/A |
| Calyx color (RHS No.) | 134C | 134C | 134C |
| Stigma shape | Filiform | Filiform | N/A |
| Stigma length | ⅛ in at day 17 | N/A | N/A |
| Stigma color (RHS No.) | 155D | N/A | N/A |
| Corolla shape | Ovular | Ovular | Round |
| Corolla size | 0.6-0.8 mm | 0.2-0.4 mm | 0.6-0.8 mm |
| Corolla color (RHS No.) | N144C | 143B | 145A |
| Trichome shape | Bulbous | N/A | N/A |
| Trichome color (RHS No.)(at harvest) | 155D | N/A | N/A |
| Other types of trichomes | Capitate-stalked | N/A | N/A |
| Terminal bud shape | Pyramidal | N/A | N/A |
| Terminal bud color (RHS No.) | 142A | N/A | N/A |
| Pedicel | N/A | N/A | N/A |
| Staminate shape | N/A | N/A | N/A |
| Pollen description | N/A | N/A | Microspores; Small grain/ yellowish green |
| Seed shape | Oblong; Reniform | Oblong; Reniform | Oblong; Reniform |
| Seed size/ length | 2-4 mm | 2-4 mm | 2-4 mm |
| Marbling of seed | None | None | None |
| Petal description | Symmetrical | N/A | N/A |
| Petal arrangement | Whorled | N/A | N/A |
| Max THC content | 7.1% | 1.02% | N/A |
| Max CBD content | 11.0% | 20.03% | N/A |

The new variety of *Cannabis* plant shares several similarities with the parental varieties, such as flowering habits, inflorescence position, and bract shape, size, and color. However, there are noticeable differences as well. The flower arrangement of the new variety is compact, dense, and strobilus, compared to the open, spread out, and strobilus shape of the female parental variety, 'AC/DC', and the actinomorphic shape of the male parental variety 'Redneck Wedding'. In terms of the number of flowers per plant, the new variety produces slightly fewer flowers, with 40-50 per plant, while the female parental variety produces 50-60, and the male variety produces over 1000 flowers per plant.

The new variety also has unique measurements for individual pistillate length (⅜ in at day 17) and flower diameter (¾ in at day 17), as well as a distinctive corolla shape (ovular) and size (0.6-0.8 mm) compared to the female parental variety (0.2-0.4 mm). Furthermore, it exhibits bulbous trichome shape and a pyramidal terminal bud shape, with a terminal bud color of RHS No. 142A.

When it comes to cannabinoid content, the new variety has a maximum THC content of 7.1% and a maximum CBD content of 11.0%. This is different from the female parental variety, which has a lower maximum THC content of 1.02% and a higher CBD content of 20.03%. The male parental variety does not have available data on THC and CBD content.

While leaf, stem, and inflorescence morphology are important features of *Cannabis* plants, there are other characteristics that can also provide valuable insights into a cultivar's growth habits and potential uses. In Table 6, below, a comprehensive breakdown of additional miscellaneous characteristics of the new cultivar, as well as its parent plants, is shown. The detailed analysis of these characteristics presented in this table allows growers and enthusiasts to better understand and appreciate the unique properties of this cultivar. The cultivar's diverse set of characteristics make it an attractive choice for a range of applications, including, but not limited to, medicinal *Cannabis* markets. This new and distinct *Cannabis* cultivar is expected to have a significant impact on the industry and may become a leading player in the global *Cannabis* market.

TABLE 6

Other Characteristics

| Characteristics | New Variety | Parental Variety ('AC/DC') (Female Plant) | Parental Variety ('Redneck Wedding') (Male Plant) |
|---|---|---|---|
| Time period and condition of flowering/blooming | 56 days | 56 days | 28 to 56 days |
| Hardiness of plant | High | High | High |
| Breaking action | Flexible | Flexible | Flexible |
| Rooting rate after cutting/cloning | 95% | 95% | 95% |
| Types of cutting for cloning (stem, leaf, root, etc.) | Stem | Stem | Stem |
| Shipping quality if available | Hardy | Hardy | Hardy |
| Storage life if available | N/A | N/A | N/A |
| Productivity of flower if available | N/A | N/A | N/A |
| Market use | Medicinal | N/A | N/A |

The new variety and the parental variety, 'AC/DC', have a similar time period and condition of flowering/blooming of 56 days, while the male parental variety, 'Redneck Wedding', has a shorter period of 28 to 56 days. The hardiness of all three varieties is high, and their breaking action is flexible. The rooting rate after cutting/cloning is 95% for all three varieties, and stem cutting is the method used for cloning. The shipping quality and storage life are not available, and the productivity of flower is not applicable. The market use of the new variety is medicinal, while the parental varieties do not have a specified market use in the table.

The following is a detailed description of the new cultivar of 'AC/DC x Redneck Wedding 13'. The following description is for plants that are 17-55 days old as of the time of the measurements.

General description:

Classification:

*Denomination.*—'AC/DC x Redneck Wedding 13'.

*Species.*—*Cannabis* hybrid.

Origin, form, and growth characteristics:

*Origin.*—'AC/DC' x 'Redneck Wedding'; Seed.

*Propagation.*—Asexual propagated by cloning, stem cuttings.

*Propagation ease.*—Easy.

Plant:

*Height.*—16 in at 17 days (vegetative stage); 55 in (flowering).

*Width.*—14 in at 17 days (vegetative stage); 26 in. (flowering).

*Vigor.*—Moderate.

*Pest resistance.*—Good.

*Disease susceptibility.*—Below Average; Resistant.

*Time to harvest.*—55 days.

*Time to root.*—9 days.

*Genetically modified organism.*—No.

Leaf/foliage:

*Structure.*—Linear lanceolate leaflets; thin leaflets with minimal curl and minimal concavity.

*Shape.*—Palmately compound with five main leaflets and two rear leaflets.

*Arrangement.*—Normal spiraling; Alternate with average node spacing of 1.5 in at 17 days old.

*Margin.*—Spread of 1.5 in to 2 in between apex of leaflets.

*Serration.*—Deep serration; spread of approximately 5 mm.

*Hair.*—Not visually present; Extremely fine.

*Leaf (with petiole) length at maturity.*—8-10 inches.

*Leaf width at maturity.*—5 in.

*No. of leaflets.*—7.

*Middle largest (longest) leaflet length.*—5 in.

*Middle largest (longest) leaflet width.*—1.5 in.

*Middle largest (longest) leaflet length/width ratio.*—10:3.

*No. teeth of middle leaflet (average).*—45.

*Leaf color (upper side).*—135C.

*Leaf color (lower side).*—135D.

*Leaf glossiness.*—Matte.

*Vein/midrib shape.*—Centrally located; Narrow-shallow on top; thick and round on underside with a depth of medium to deep.

*Vein/midrib color.*—137D.

Petiole:

*Petiole length.*—3 in to 5 in.

*Petiole color.*—59C.

*Intensity of petiole anthocyanin.*—Average (vegetative stage); Intense (late flowering stage).

*Stipule length.*—0.5 in at 17 days old.

*Stipule shape.*—Linear-lanceolate, with a narrowing tip and slight curvature.

*Stipule color.*—134D.

Stem:

*Shape.*—Rounded; ribbed.

*Diameter.*—0.25 in at 17 days old (vegetative stage); 1.5 in-2 in (flowering).

*Color.*—137C.

*Strength.*—High.

*Texture.*—Smooth, slight elevations and raised nodules, fine hairs.

*Depth of main stem ribs/grooves.*—Medium to Deep.

*Internode length.*—2 in.

*Stem branching.*—Monopodial.

*Node spacing.*—1.5 in to 2 in.

Inflorescence:

*Blooming/flowering habit.*—Indoors, blooming stage, the female *Cannabis* plant undergoes a critical transition from vegetative growth to reproductive development, triggered by photoperiodic cues, 12 hours daylight/12 hours darkness. The plant begins to produce small, white pistils at the nodes where the leaves meet the stem, which develop into mature flowers.

*Inflorescence position relative to foliage.*—Apical meristem.

*Flower arrangement.*—Raceme.

*No. of flowers per plant.*—40 to 50.

Flower:

*Shape.*—Compact; dense; Strobilus.

*Flower (individual pistillate length).*—3 in to 4 in.

*Flower (raceme) diameter.*—2 in to 3 in.

*Corolla shape.*—Ovular.

*Corolla size.*—0.6-0.8 mm.

*Corolla color.*—N144C.

*Bract shape.*—Obovate.

*Bract size.*—¼ in at day 17.

*Bract color.*—140A.

*Stigma shape.*—Filiform.

*Stigma length.*—⅛ in at day 17.

*Stigma color.*—155D.

*Trichome shape.*—Bulbous.

*Trichome color.*—155D.

*Other types of trichome.*—Capitate-stalked.

*Cola (terminal bud).*—Pyramidal.

*Cola (terminal bud) color.*—142A.

*Pedicel.*—N/A.

*Pedicel color.*—N/A.

*Staminate flower.*—N/A.

*Pollen.*—N/A.

*Seed shape.*—Oblong; Reniform.

*Seed size/length.*—2 to 4 mm.

*Marbling of seed.*—None.

*Petal.*—Symmetrical.

*Petal arrangement.*—Whorled.

Other characteristics:

*Aroma.*—Mild, slightly vinegar in leaf but strong and sweet in stem.

*Flowering/blooming period.*—56 days.

*Hardiness.*—High.

*Breaking action.*—Flexible.

*Rooting rate after cutting/cloning.*—95%.

*Types of cutting for cloning.*—Stem.

*Shipping quality.*—Hardy.

*Storage life.*—N/A.

*Productivity of flower.*—N/A.

*Market use.*—Medicinal.

The above new and distinct cultivar, 'AC/DC x Redneck Wedding 13,' is distinguishable from related cultivars in that it exhibits unique leaf characteristics, balanced THC and CBD levels, a pleasant aroma and taste, an upright monopodial growth habit, and tight, compact flowering. This new variety displays large leaves with deep serrations, offering a symmetrical and visually appealing structure. Additionally, the leaves are known for their dark color, which contributes to the plant's overall aesthetic.

One of the key features that sets the 'AC/DC x Redneck Wedding 13' cultivar apart from prior and related cultivars is its balanced THC and CBD levels. This characteristic allows for a more desirable combination of medicinal properties, catering to a broader range of users and applications. A more balanced ratio of THC and CBD offers significant medicinal benefits, as it can provide effective relief for various symptoms and conditions without inducing an overwhelming psychoactive effect.

The pleasant aroma and taste associated with this new variety further differentiate it from its predecessors, making it more appealing to both growers and consumers. These sensory attributes can play a crucial role in the overall enjoyment and satisfaction derived from the plant, contributing to its marketability and popularity.

Another noteworthy aspect of the 'AC/DC x Redneck Wedding 13' cultivar is its upright monopodial growth habit. This growth pattern provides several advantages, including efficient use of vertical space, improved light penetration, improved air circulation, and easier pruning and maintenance. The monopodial growth habit allows for more effective light distribution throughout the plant, which can lead to increased photosynthesis and energy production. As a result, this cultivar can potentially produce higher yields compared to plants with other growth patterns. Lastly, the tight and compact flowering of this new cultivar sets it apart from related varieties. The dense floral structure not only contributes to the plant's visual appeal but can also result in higher concentrations of active compounds and a more potent final product.

When compared to the known *Cannabis* cultivars, such as *Cannabis* cultivars denoted as 'LEMON CRUSH OG' (U.S. Plant Pat. No. PP31,535 P3) and 'UNIQUE FLOWER ORIGINAL HAZE' (U.S. Plant Pat. No. PP34,802 P2), 'AC/DC x Redneck Wedding 13' exhibits a balanced THC: CBD profile. Specifically, 'AC/DC x Redneck Wedding 13' exhibits approximately 7.1% THC and approximately 11% CBD; whereas 'LEMON CRUSH OG' exhibits approximately 18.77-23.19% THC and approximately 0.00% CBD and 'UNIQUE FLOWER ORIGINAL HAZE' exhibits approximately 17.38% THC and approximately 0.1% CBD. As a result, the balances terpene profile of 'AC/DC x Redneck Wedding 13' makes it a more desirable medicinal *Cannabis* cultivar for providing increase medicinal benefit without the psychoactive effect typically exhibited by *Cannabis* cultivar with high THC and low CBD content. In terms of leaf characteristics, 'AC/DC x Redneck Wedding 13' appears more uniformly spread with a more balanced overall length to width ration of the entire leaf than that of 'LEMON CRUSH OG' which appears elongated. As compared to 'UNIQUE FLOWER ORIGINAL HAZE', 'AC/DC x Redneck Wedding 13' has less leaflets and wider leaflets than the known cultivar. Additionally, 'AC/DC x Redneck Wedding 13' has deeper serrations with more teeth than 'LEMON CRUSH OG' and 'UNIQUE FLOWER ORIGINAL HAZE' making it more aesthetically pleasing and a more desirable cultivar.

Overall, the unique combination of leaf characteristics, balanced cannabinoid levels, pleasant aroma and taste, upright monopodial growth habit, and tight, compact flowering make the 'AC/DC x Redneck Wedding 13' cultivar a distinguishable and superior choice compared to prior and related *Cannabis* cultivars known to the Inventor. The potential for higher yields, combined with the medicinal benefits offered by balanced THC and CBD levels, make this cultivar particularly advantageous for both growers and consumers seeking a versatile and effective *Cannabis* strain.

The invention claimed is:

1. A new and distinct cultivar of *Cannabis* plant named 'AC/DC x Redneck Wedding 13' substantially as shown and described herein.

* * * * *